(12) United States Patent  
Houben et al.

(10) Patent No.: US 8,744,559 B2  
(45) Date of Patent: Jun. 3, 2014

(54) METHODS, SYSTEMS AND DEVICES FOR DETECTING ATRIAL FIBRILLATION

(76) Inventors: Richard P. Houben, Lanaken (BE); Vincent C. Larik, Kerkrade (NL); Robert G. Tieleman, Haren (NL)

( * ) Notice: Subject to any disclaimer, the term of this patent is extended or adjusted under 35 U.S.C. 154(b) by 177 days.

(21) Appl. No.: 13/208,211

(22) Filed: Aug. 11, 2011

(65) Prior Publication Data

US 2013/0041273 A1    Feb. 14, 2013

(51) Int. Cl.  
*A61B 5/0404* (2006.01)

(52) U.S. Cl.  
USPC .......................................... 600/518; 600/519

(58) Field of Classification Search  
USPC .................................................. 600/518, 519  
See application file for complete search history.

(56) References Cited

U.S. PATENT DOCUMENTS

| | | | |
|---|---|---|---|
| 5,337,753 A * | 8/1994 | Lekhtman | 600/519 |
| 5,620,471 A * | 4/1997 | Duncan | 607/14 |
| 6,104,296 A | 8/2000 | Yasushi et al. | |
| 6,149,602 A | 11/2000 | Arcelus | |
| 6,490,479 B2 | 12/2002 | Bock et al. | |
| RE38,515 E | 5/2004 | White | |
| 6,871,089 B2 | 3/2005 | Korzinov et al. | |
| 7,146,206 B2 | 12/2006 | Glass et al. | |
| 7,283,870 B2 | 10/2007 | Kaiser et al. | |
| 7,308,301 B2 | 12/2007 | Povinelli et al. | |
| 7,353,057 B2 | 4/2008 | Schiessle et al. | |
| 7,596,405 B2 | 9/2009 | Kurzweil et al. | |
| 7,627,368 B2 | 12/2009 | Houben et al. | |
| 7,630,756 B2 | 12/2009 | Linker | |

(Continued)

FOREIGN PATENT DOCUMENTS

DE    10 2006 057882    8/2006  
EP    1602326    7/2006

(Continued)

OTHER PUBLICATIONS http://ecgmonitor.org/buy-handheld-ecg/#7 >; Buy Handheld ECG.

(Continued)

*Primary Examiner* — Christopher D Koharski  
*Assistant Examiner* — Michael Carey  
(74) *Attorney, Agent, or Firm* — Woods Patent Law

(57) ABSTRACT

Disclosed herein are various embodiments of methods, systems and devices for detecting atrial fibrillation (AF) in a patient. According to one embodiment, a patient places his or her left and right hands around left and right electrodes and a hand-held atrial fibrillation detection device acquires an electrocardiogram (ECG) from the patient over a predetermined period of time such as, by way of example, one minute. After acquiring the ECG from the patient, the device processes and analyzes the ECG and makes a determination of whether the patient has AF. The device may further be configured to provide a visual or audio indication of whether the patient has AF, or does not have AF. The device may be employed in a health care provider's office without the need for complicated or expensive diagnostic equipment, and is capable of providing an on-the-spot and low-cost diagnosis of AF. The device may further be connected to a physician's computer in the office, which may be configured to store the results of the analysis and the patient's ECG, and which may further be configured to carry out additional processing and analyses of the acquired and processed data. Moreover, the physician's computer may be operably connected to a remote server configured to store, process and analyze the ECG and the results provided by the hand-held device.

19 Claims, 26 Drawing Sheets

(56) References Cited

U.S. PATENT DOCUMENTS

| | | | |
|---|---|---|---|
| 7,634,310 | B2 | 12/2009 | Lee et al. |
| 2002/0065473 | A1 | 5/2002 | Wang et al. |
| 2003/0144597 | A1 | 7/2003 | Bock |
| 2004/0230109 | A1 | 11/2004 | Schiessle et al. |
| 2005/0004483 | A1 | 1/2005 | Lin |
| 2005/0165320 | A1 | 7/2005 | Glass et al. |
| 2006/0009698 | A1 | 1/2006 | Banet et al. |
| 2006/0276716 | A1 | 12/2006 | Healey et al. |
| 2007/0073177 | A1* | 3/2007 | Kontothanassis et al. .... 600/518 |
| 2010/0010360 | A1 | 1/2010 | Kurzweil |
| 2010/0076331 | A1 | 3/2010 | Chan et al. |

FOREIGN PATENT DOCUMENTS

| | | |
|---|---|---|
| WO | WO 02/056961 | 7/2002 |
| WO | WO 03/105020 | 12/2003 |
| WO | WO 2004/071576 | 8/2004 |
| WO | WO 2006/045065 | 4/2006 |
| WO | WO 2007/050229 | 5/2007 |
| WO | WO 2008/007236 | 1/2008 |
| WO | 2009/087350 A1 | 7/2009 |
| WO | WO 2009/090581 | 7/2009 |
| WO | 2013/020710 A1 | 2/2013 |

OTHER PUBLICATIONS http://europace.oxfordjournals.org/content/11/10/1362.full; Prospective, Multicentre Validation of a Simple, Patient-Operated Electrocardiographic System for the Detection of Arrhythmias and Electrocardiographic Changes.

https://www.favoriteplus.com/instantcheck-handheld-ecg-ekg-monitor-fp-ich.php; Handheld ECG-EKG Monitor.

www.ncbi.nlm.nih.gov/.../11804173; Tateno K, Glass L; Automatic Detection of Atrial Fibrillation Using the Coefficient of Variation and Density Histograms of RR and deltaRR Intervals.

www.ncbi.nlm.nih.gov/.../21419421; Winkler S, Axmann C, et al.; Diagnostic Accuracy of a New Detection Algorithm for Atrial Fibrillation in Cardiac Telemonitoring with Portable Electrocardiogram Devices.

IEEE Transactions on Biomedical Engineering, vol. BME-32, No. 3, Mar. 1985; Jiapu Pan and Willis J. Tompkins, A Real-Time QRS Detection Algorithm.

Moody et al., "A New Method for Detecting Atrial Fibrillation Using R-R Intervals," Computers in Cardiology, 1983, IEEE, 0276-6574/83/0000/0227.

Young et al., "A comparative study of a hidden Markov model detector for atrial fibrillation," Neural Networks for Signal Processing IX, 1999. Proceedings of the 1999 IEEE Signal Processing Society Workshop, Madison, WI. USA Aug. 23-25, 1999 Aug. 23, 1999, pp. 468-476, XP010348490, DOI: 10.1109/NNSP, 1999.788166; ISBN: 978-0-7803-5673-3.

Tuemer et al., "A syntactic methodology for automatic diagnosis by analysis of continuous time measurements usinh hierarchical signal representations," IEEE Transactions on Systems, Man and Cybernetics. Part B: Cybermetics, vol. 33, No. 6, Dec. 1, 2003, pp. 951-965, XP 011103623, ISSN: 1083-4419, DOI: 10.1109/TSMCB.2002.804365 section "V. Example: ECG Diagnosis".

Andreao et al., "ECG Signal Analysis through Hidden Markov Models," IEEE Transactions on Biomedical Engineering, vol. 53, No. 8, Aug. 1, 2006, pp. 1541-1549, XP55030287, ISSN: 0018-9294, DOI: 10.119/TBME.2006.877103 sections "III. Automatic Beat Segmentation and Classification" and "V. Condusion.".

Petrucci et al., "Atrial Fibrillation Detection Algorithms for Very Long Term ECG Monitoring," Computers in Cardiology, 2005; 32: 623-626.

Ghodratgi et al., "RR Interval Analysis for Detection of Atril Fibrillation in ECG Monitors," 30th Annual International IEEE EMBS Conference, Vancouver, BC, Canada, Aug. 20-24, 2008.

* cited by examiner

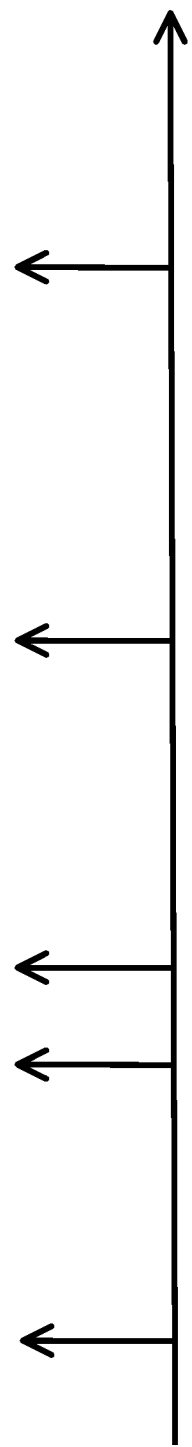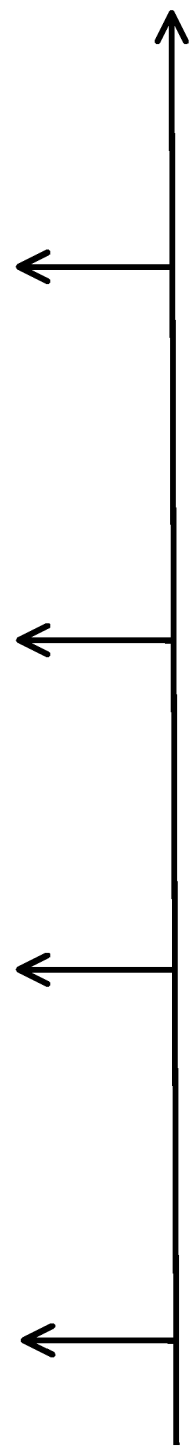

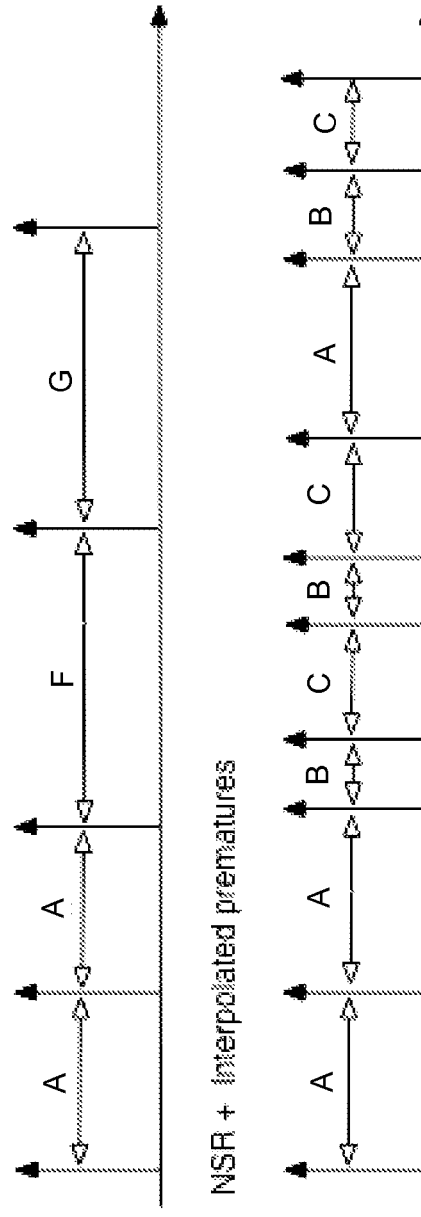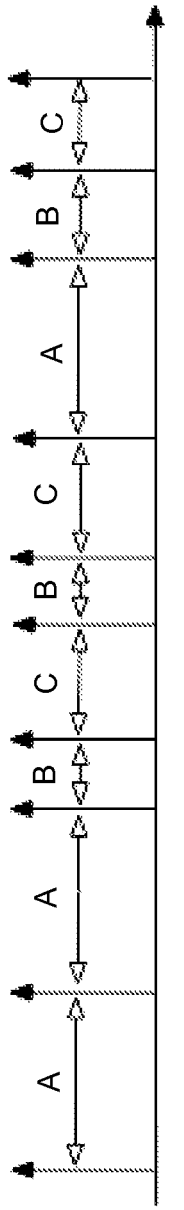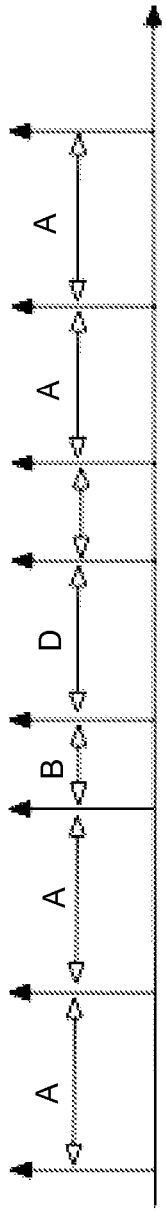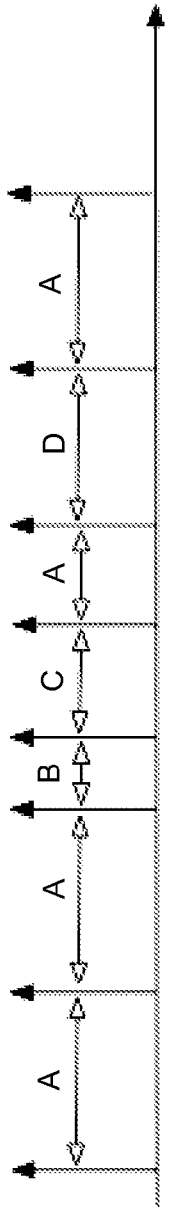
FIG. 27 Episode Pre-Recognition — Rhythm Change Fast to Slow
FIG. 28 NSR + Interpolated prematures
FIG. 29 NSR + Non-Interpolated Prematures
FIG. 30 NSR + Interpolated + Noninterpolated prematures

US 8,744,559 B2

METHODS, SYSTEMS AND DEVICES FOR DETECTING ATRIAL FIBRILLATION

FIELD

Various embodiments described herein relate to the field of detecting cardiac arrhythmias in patients, and methods, components, devices and systems therefor.

BACKGROUND

Atrial fibrillation (or AF) is the most common cardiac arrhythmia or abnormal heart rhythm suffered by human patients. AF develops in the two upper chambers or atria of the heart, and is so-named owing to the fibrillation or quivering of the heart muscles of the atria (as opposed to the normal coordinated contraction of the atria). Patients suffering from AF often have heartbeats that do not occur at regular intervals, or they may present an absence of normal P-waves in their electrocardiograms (ECGs). The risk of AF increases with age, and it is estimated that 8% of people over 80 suffer from AF.

In AF, the normal electrical impulses generated by the sino-atrial (SA) node are overwhelmed by disorganized electrical impulses that originate in the atria and pulmonary veins, leading to the conduction of irregular impulses to the ventricles that generate a heartbeat. The result is an irregular heartbeat, which may occur in episodes lasting from minutes to weeks, or that may occur continuously over a period of years. Atrial fibrillation has a pronounced tendency AF to become chronic, which in turn leads to an increased risk of severe health consequences such as cerebrovascular accident (CVA, or stroke) and death.

Atrial fibrillation is often asymptomatic, and in the general case is not life-threatening. Atrial fibrillation can result in palpitations, fainting, chest pain, congestive heart failure, and a generally decreased quality of life. Patients suffering from AF usually have a significantly increased risk of stroke (up to seven times that of the general population). Stroke risk increases during AF because blood may pool and form clots in the poorly contracting atria, especially in the left atrial appendage (LAA). Atrial fibrillation is known to be a leading cause of stroke.

Detecting or diagnosing AF in a patient typically requires the acquisition, processing and analysis of ECGs from the patient, which in turn usually involves the employment of complicated, costly and specialized medical equipment. Such medical equipment is often unavailable to or too costly for general practitioners and health care providers. Moreover, such medical equipment must often be operated by medical specialists, which further decreases the possibility of widespread and effective diagnosis of AF among the general population. Given the prevalence of AF in the general population, and the serious and debilitating consequences of AF, what is needed is a more economic, easier and quicker means of diagnosing AF in patients, especially in the context of patients visiting their general practitioner or health care provider.

SUMMARY

In one embodiment, there is provided a method of detecting atrial fibrillation in an electrocardiogram (ECG) acquired from a patient comprising determining times corresponding to R-waves in the electrocardiogram, determining a plurality of sequentially-ordered R-R time intervals corresponding to the R-wave times, selecting an R-R test interval (INT) from among the plurality of R-R time intervals, sequentially selecting the R-R time intervals and comparing same in a base rhythm recognition state machine to determine which of the selected R-R time intervals correspond to at least one of a predetermined number of non-atrial-fibrillation states, at least some of the non-atrial-fibrillation states requiring updating of INT when R-R time intervals are compared therein, and further determining which of the selected R-R time intervals correspond to a potential atrial fibrillation state; generating, on the basis of the selected and compared R-R time intervals, a base cardiac rhythm score.

According to another embodiment, there is provided a device configured to detect atrial fibrillation in a patient comprising first and second electrodes configured to sense electrocardiograms (ECGs) of the patient, amplifier circuitry configured to receive and amplify the ECGs, at least one processor configured to detect times corresponding to R-waves in the ECGs, determine sequentially-ordered R-R time intervals corresponding to the R-wave times, select an R-R test interval (INT) from among the plurality of R-R time intervals, sequentially select the R-R time intervals and compare same in base rhythm recognition state machine to determine which of the selected R-R time intervals correspond to at least one of a predetermined number of non-atrial-fibrillation states, at least some of the non-atrial-fibrillation states requiring updating of INT when R-R time intervals are compared therein, determine which of the selected R-R time intervals correspond to a potential atrial fibrillation state, and generate, on the basis of the selected and compared R-R time intervals, a base cardiac rhythm score.

Further embodiments are disclosed herein or will become apparent to those skilled in the art after having read and understood the specification and drawings hereof.

BRIEF DESCRIPTION OF THE DRAWINGS

Different aspects of the various embodiments of the invention will become apparent from the following specification, drawings and claims in which:

FIGS. 18(a) and 18(b) illustrate the results of a method of pre-processing R-R intervals;

FIGS. 22-30 illustrate examples of chains and chain lengths generated by the base rhythm recognition state machine of FIG. 19 according to various patient cardiac conditions;

The drawings are not necessarily to scale. Like numbers refer to like parts or steps throughout the drawings, unless otherwise noted.

DETAILED DESCRIPTIONS OF SOME EMBODIMENTS

Figure 1:
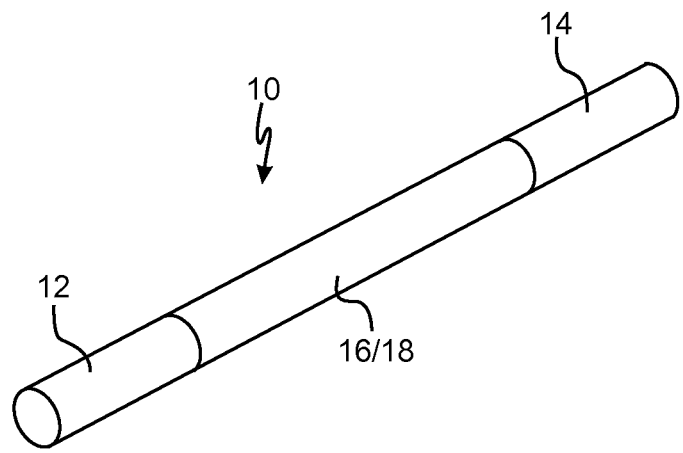
FIG. 1 shows one embodiment of a hand-held atrial fibrillation detection device.

In the following description, specific details are provided to impart a thorough understanding of the various embodiments of the invention. Upon having read and understood the specification, claims and drawings hereof, however, those skilled in the art will understand that some embodiments of the invention may be practiced without hewing to some of the specific details set forth herein. Moreover, to avoid obscuring the invention, some well known methods, processes and devices and systems finding application in the various embodiments described herein are not disclosed in detail.

In the drawings, some, but not all, possible embodiments are illustrated, and further may not be shown to scale.

FIG. 1 shows one embodiment of a hand-held atrial fibrillation detection device 10 comprising first electrode 12, second electrode 14, housing 16, and light pipe 18 having visual indicator 20 (not shown in FIG. 1) disposed therewithin. Device 10 is configured for a patient to hold first electrode 12 in one hand and second electrode 14 in the other hand. Electrodes 12 and 14 are separated by device housing 16, which in one embodiment comprises electrically non-conductive material that prevents the sensing of ECGs from being adversely affected. Electrodes 12 and 14 may be formed of any suitable electrically conductive material such as metal or a metal alloy. While the patient holds device 10, the device acquires electrocardiogram (ECG) data from the patient through the first and second electrodes 12 and 14 over a predetermined period of time (e.g., 60 seconds). Once device 10 has successfully acquired ECG data from the patient, the acquired ECG data are processed and analyzed using circuitry and electronics disposed therewithin. According to one embodiment, and after the ECG data have been acquired, processed and analyzed, device 10 is configured to provide a visual, audio and/or tactile feedback indication of whether a normal cardiac rhythm has been detected on the one hand, or atrial fibrillation has been detected on the other hand. For example, light pipe 18 of device 10 may be formed of a transparent material such as plastic and have visual indicators such as LEDs housed therein. If a normal cardiac rhythm in the patient has been detected by device 10, green LEDs in housing 16 and light pipe 18 are activated to provide a visual indication that the patient's does not suffer from atrial fibrillation. If atrial fibrillation in the patient has been detected by device 10, red LEDs in housing 16 and light pipe 18 are activated to provide a visual indication that the patient's does suffer from atrial fibrillation. Other visual, audio and tactile feedback methods and devices are also contemplated, as those skilled in the art will now appreciate.

Continuing to refer to FIG. 1, device 10 is one embodiment of the "MyDiagnostick"™ device intended to discriminate between atrial fibrillation (AF) and normal cardiac rhythms (or normal sinus rhythms) in a patient. The MyDiagnostick™ device is employed to screen large patient populations who are at risk for AF and associated complications like stroke. The MyDiagnostick™ device is a portable, hand-held, low-cost device that can be used by patients and health care providers such as general practitioners, nurses and cardiologists. The MyDiagnostick™ device can be used at any time and in virtually any place simply by having a patient hold the device in both hands for a predetermined period of time until the results of the screening session are revealed. According to one embodiment, and as described above, at the end of the screening session light pipe 18 of the MyDiagnostick™ device turns green to indicate a normal cardiac rhythm or turns red in to indicate that the patient suffers from atrial fibrillation (AF). In addition, device 10 can be configured for use by a patient outside a physician's or health care provider's office. Under such circumstances, if device 10 detects AF the patient can contact his or her physician to conduct a more detailed diagnosis for AF.

Continuing to refer to FIG. 1, and according to one embodiment, device 10 features no buttons or controls disposed on the exterior surface thereof for manipulation by a patient. This is because device 10 is dedicated to performing a single diagnostic test for AF only. Device 10 can be configured to switch on automatically when it is picked up from a rest position by means of, for example, an accelerometer or motion detector that activates device 10 when device 10 is moved or picked up. Moreover, device 10 can be configured to switch off automatically after it has delivered its diagnostic results or not been moved or touched for a predetermined period of time (e.g., ten minutes) using, for example, an accelerometer or motion detector that turns off device 10 when device 10 has not been moved or picked up for the predetermined period of time, or that turns device 10 off after the diagnostic results have been provided. In one embodiment, the time period for device 10 to render a diagnosis of AF or no AF is set at one minute or less.

Note that in one embodiment device 10 is a hand-held device, although in other embodiments device 10 may be a stationary or semi-stationary device.

Figure 2:
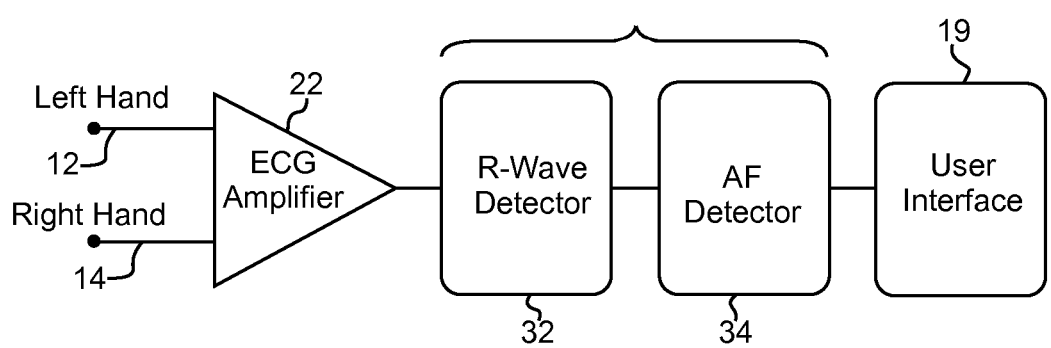
FIG. 2 shows a functional block diagram according to one embodiment of an atrial fibrillation detection device.

FIG. 2 shows a functional block diagram according to one embodiment of atrial fibrillation detection device 10. The block diagram of FIG. 2 illustrates the main functional blocks that process ECGs acquired from the patient. ECGs sensed through electrodes 12 and 14 are received by ECG amplifier circuit 22, where the ECGs are amplified and then passed on to R-wave detector 32 and AF detector 34. According to one embodiment, user interface 19 is a visual or audio indicator of AF or no AF (as described above).

Figure 3:
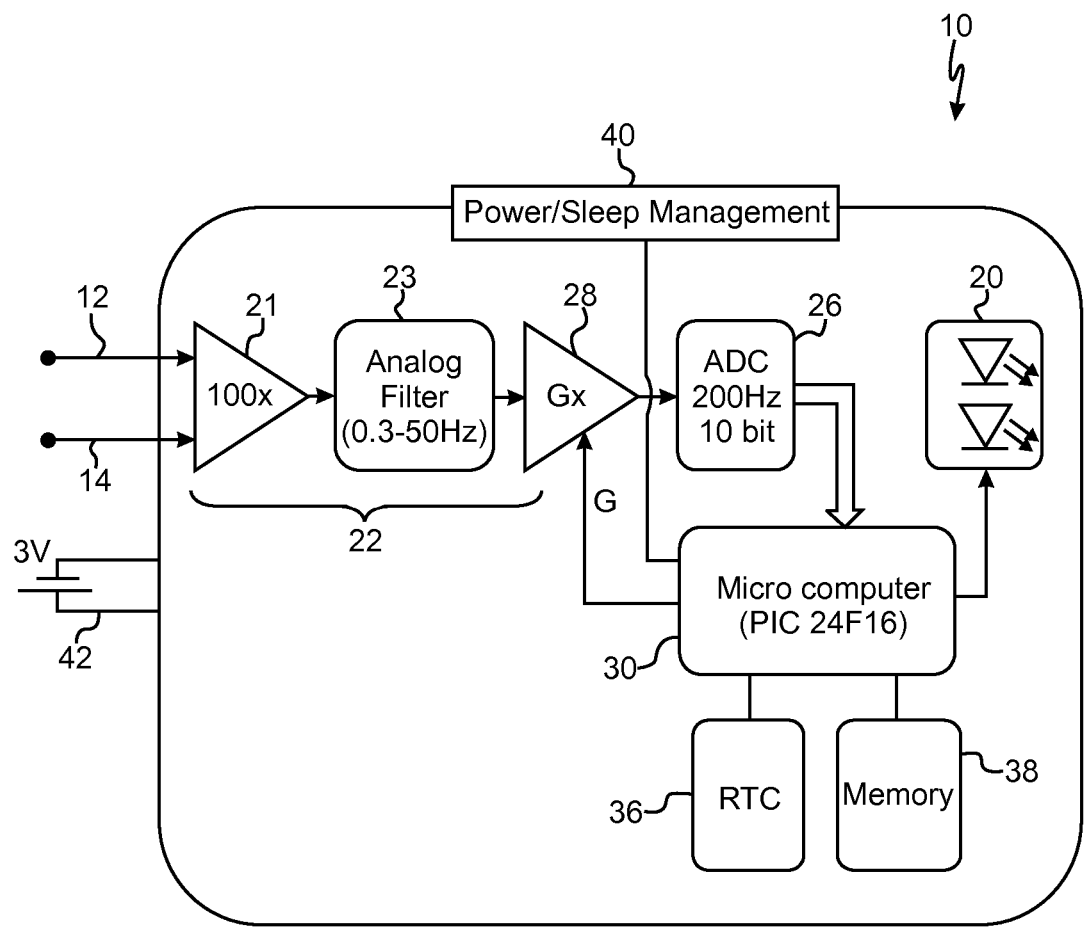
FIG. 3 shows a block circuit diagram according to one embodiment of atrial fibrillation detection device.

FIG. 3 shows a block circuit diagram according to one embodiment of atrial fibrillation detection device 10. FIG. 3 provides more technical detail regarding device 10, which according to the embodiment shown in FIG. 3 is battery-powered. In FIG. 3, device 10 features versatile power management functionality, including wake-up and power-down power/sleep management circuitry 40. Analog ECG signals, sensed through the palms of the patient through electrodes 12 and 14 are amplified by amplifier circuitry 22, which includes amplifier 21, band-pass filter 23 and transconductance amplifier 28 before being passed on to analog-to-digital converter (ADC) 26. To ensure maximum fidelity of ECG signals in the digital domain, the analog ECG signals are amplified and/or attenuated to fit the 10-bit scale of ADC 26. Further processing of ECG signals is accomplished in the digital domain by processor 30, such as R-wave detection, R-R interval determination, and AF detection, more about which is said below. Processor 30 may be any one or more of an ASIC, a controller, a micro-controller, a CPU, a processor, a micro-processor, a Peripheral Interface Controller (PIC), a digital signal processor (DSP), or any other suitable processing or computing device. The ECG data may be stored in memory 38 or any other suitable storage medium such as volatile memory, non-volatile memory, a flash drive or memory, a hard drive, or any other suitable memory or storage device for later retrieval. Processor 30 and memory 38 may also be configured to acquire and store diagnostic and performance data, which may later be employed to design or implement future product improvements. As shown in FIG. 3, and according to one embodiment, hand-held device 10 is powered by battery 42, which may be a primary or rechargeable secondary battery. In one embodiment, battery 42 is rechargeable by inductive means when placed in a docking station 44 (not shown in FIG. 3). Battery 42 may also be recharged through connection of a battery charging cable to device 10. When battery 42 is running low on available charge, device 10 can be configured to provide a low-battery indication such as by means of an LED or audio device.

Figure 4:
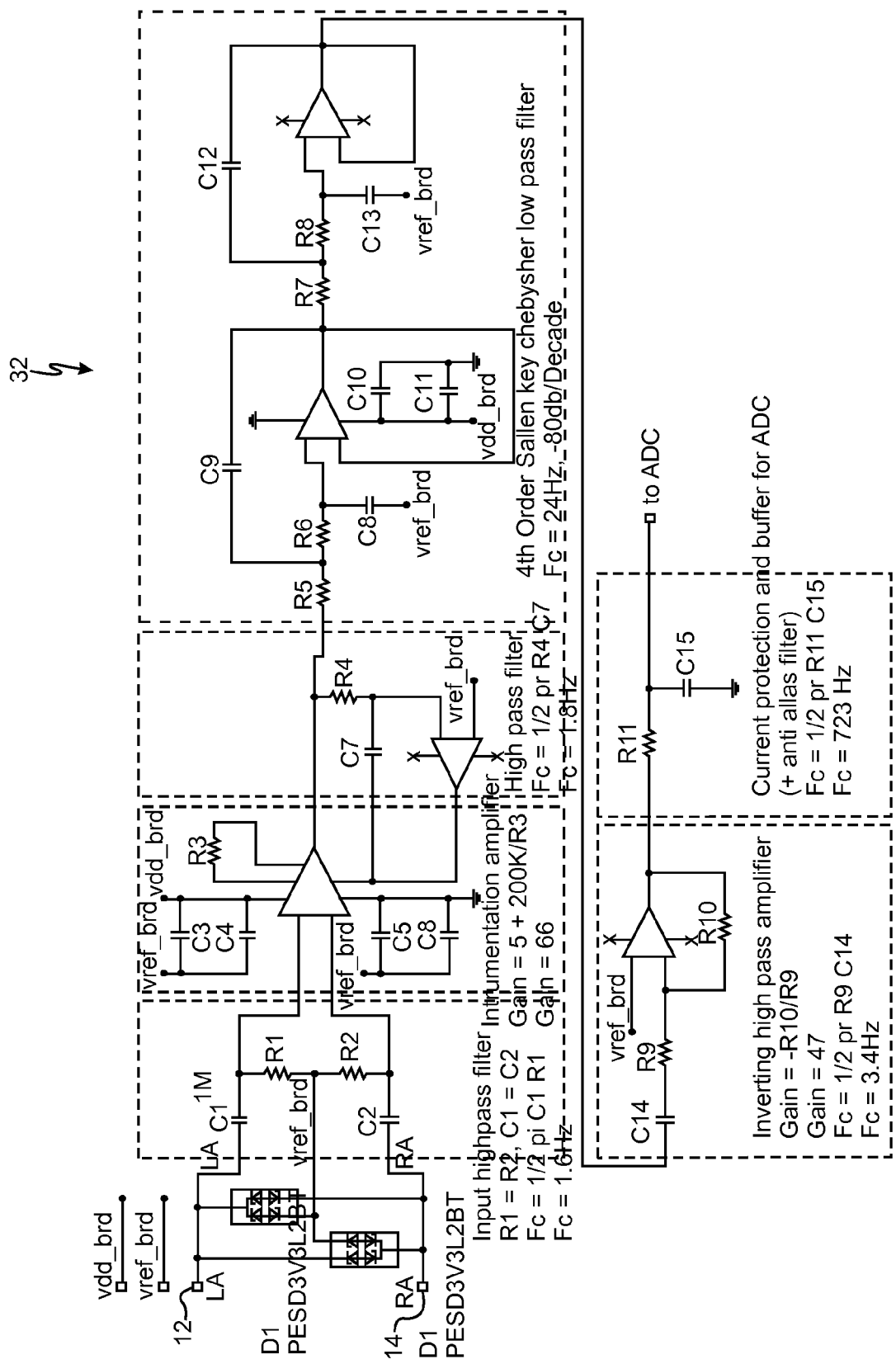
FIG. 4 shows further details according to one embodiment of circuitry associated with the hand-held atrial fibrillation detection device of FIG. 3.

FIG. 4 shows further details according to one embodiment of circuitry 22 associated with hand-held atrial fibrillation detection device 10 of FIG. 3.

Figure 5:
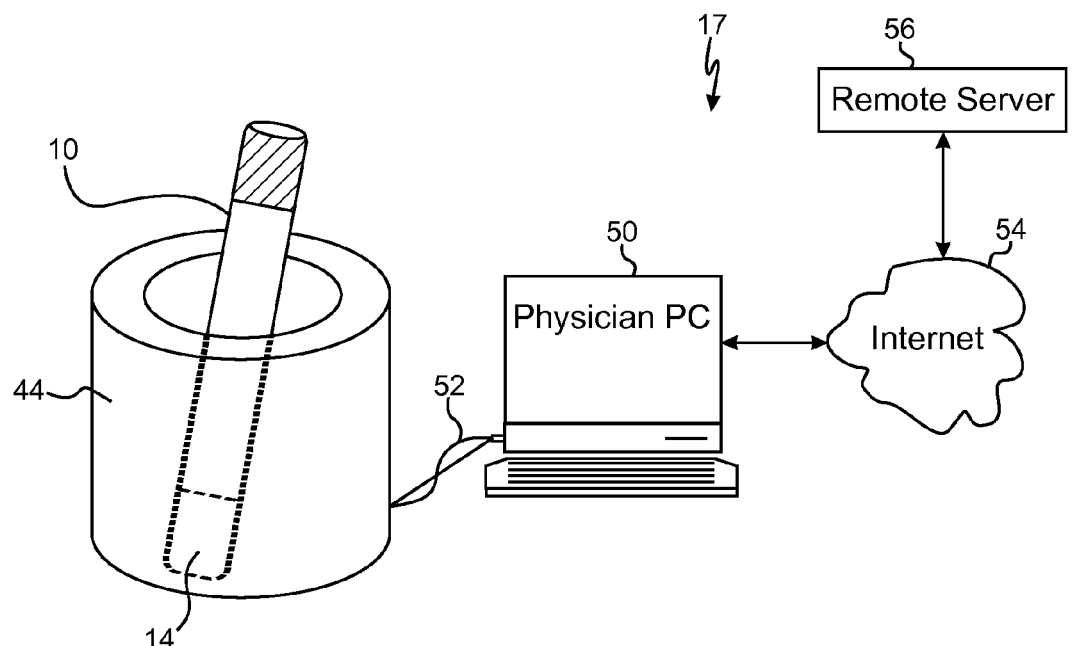
FIG. 5 shows one embodiment of an atrial fibrillation detection system.

FIG. 5 shows one embodiment of an atrial fibrillation detection system 17 comprising a hand-held atrial fibrillation detection device 10, docking station 44, physician computer 50, remote server 56 and internet 54. Device 10 may be placed in docking station 44 for battery charging when not in use by a patient, or may be placed in docking station 44 to permit downloading of ECG data that have been acquired from a patient and stored therein, where the acquired and processed data are first transferred to physician computer 50 by means of USB or other data connection 52, and then to remote server 56 by means of internet 54. Data acquired and processed by device 10 may then be stored on remote server 56 for later retrieval, and may also be subjected to further processing at remote server 56.

Figure 6:
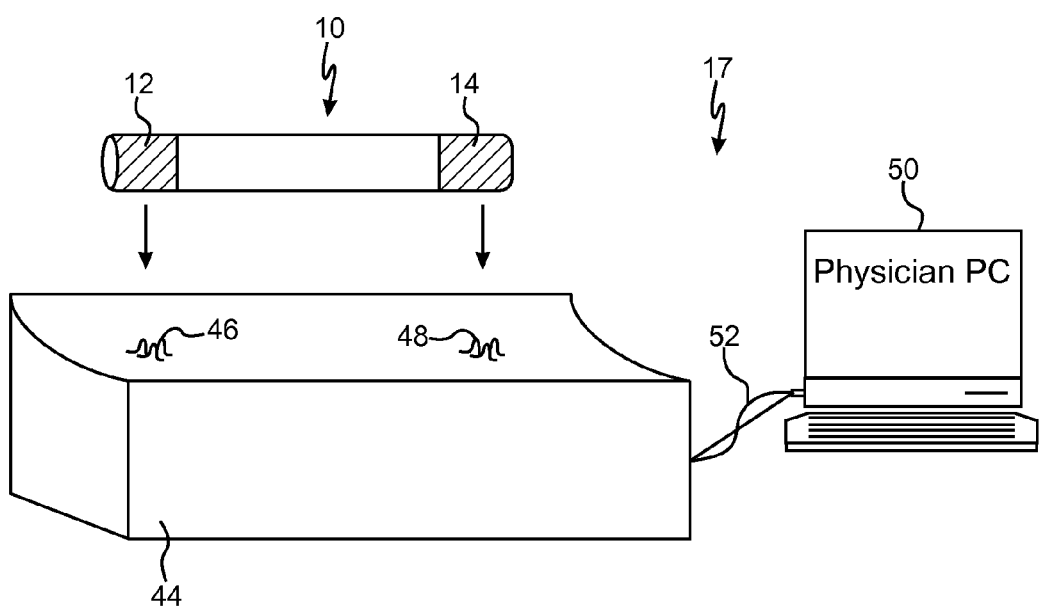
FIG. 6 shows another embodiment of an atrial fibrillation detection system.

FIG. 6 shows another embodiment of an atrial fibrillation detection system comprising a hand-held atrial fibrillation detection device 10, a docking station 44, and physician computer 50. As shown in FIG. 5, battery 42 of device 10 may be charged through contacts 46 and 48, and/or alternatively data stored in device 10 may be downloaded through contacts 46 and 48 to physician computer 50. Other embodiments and configurations for downloading data stored in device 10 and transferring same to physician computer 50 are also contemplated, such as a USB data stick configured to plug into device 10, Bluetooth or other protocol wireless transfer of data between device 10 and computer 50, MICS (Medical Implant Communications Service) protocol transfer of data, and the like.

Figure 7:
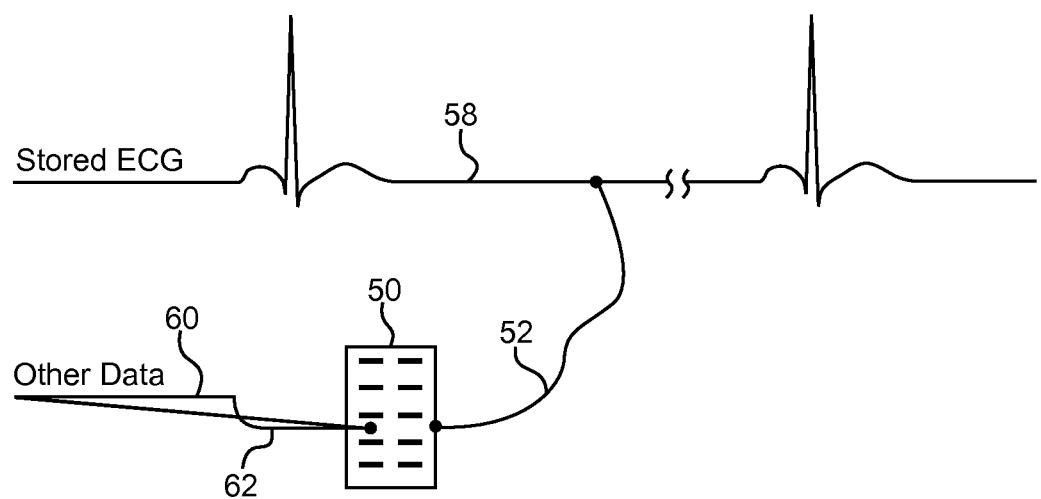
FIG. 7 shows a schematic representation of combining ECG data acquired from a patient by hand-held atrial fibrillation detection device with other data associated with the patient.
Figure 8:
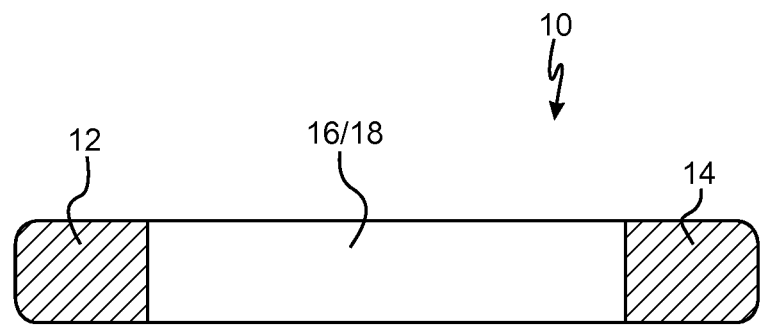
FIGS. 8-13 show various embodiments hand-held atrial fibrillation detection devices.

FIG. 7 shows a schematic representation of combining ECG data acquired from a patient by hand-held atrial fibrillation detection device 10 with other data associated with the patient, such as patient demographics, anti-arrhythmic medication, AF scores, and/or measurement dates and times. ECG data are transferred to physician computer 50 via first interface cable 52, while other data 60 are transferred to physician computer via second interface cable 62. In physician computer 50 the ECG data and the other data may be combined and/or analyzed as desired.

FIGS. 8-13 show various embodiments hand-held atrial fibrillation detection devices 10. In the embodiment of hand-held atrial fibrillation detection device 10 shown in FIG. 8, device 10 comprises an elongate cylindrically-shaped housing 16 having electrodes 12 and 14 disposed at opposite ends thereof, where electrodes 12 and 14 are configured for a patient to hold in his or her hands. Light pipe 18 is formed from a semi-transparent or transparent polymer, and permits light emitted by red and green LEDs located within housing 16 and/or light pipe 18 to be transmitted therethrough for viewing by a patient or physician, where for example the illumination of green LEDs indicates that no atrial fibrillation has been detected in the patient, and the illumination of red LEDs indicates that atrial fibrillation has been detected in the patient. The LEDs may further be configured to blink or not blink when illuminated. As described above, other means and methods are also contemplated for indicating whether or not atrial fibrillation has been detected in the patient, such as other visual displays, means and methods, and/or audio or tactile feedback means and methods.

According to one embodiment, housing 16 ranges between about ½ inch and about 2 and ½ inches in diameter, although other diameters are contemplated. Moreover, housing 16 need not be cylindrically shaped, but may assume any configuration suitable for a patient to hold and for housing the necessary electronics therewithin.

Figure 9:
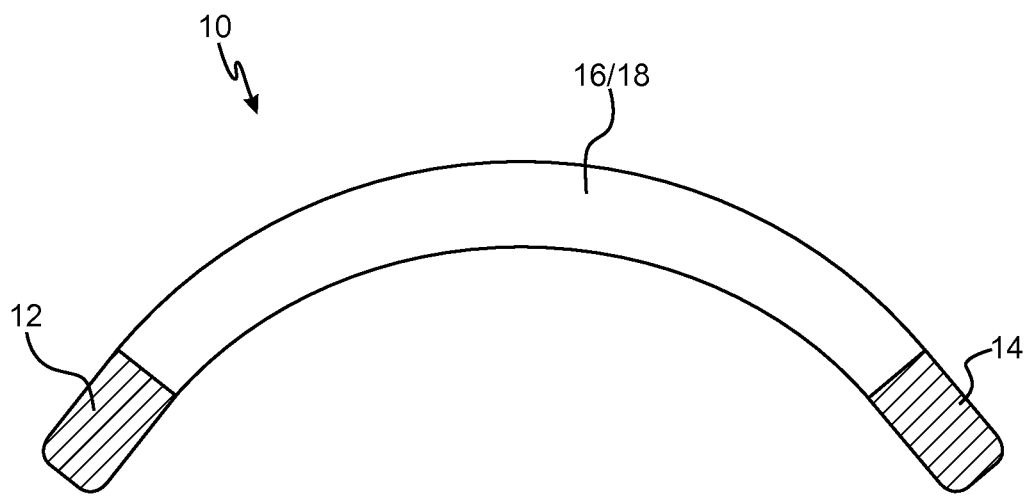

In the embodiment of hand-held atrial fibrillation detection device 10 shown in FIG. 9, device 10 comprises an elongate curved and cylindrically-shaped housing 16 having electrodes 12 and 14 disposed at opposite ends thereof, where electrodes 12 and 14 are configured for a patient to hold in his or her hands. Light pipe 18 is formed from a semi-transparent or transparent polymer, and permits light emitted by red and green LEDs located within housing 16 and/or light pipe 18 to be transmitted therethrough for viewing by a patient or physician.

Figure 10:
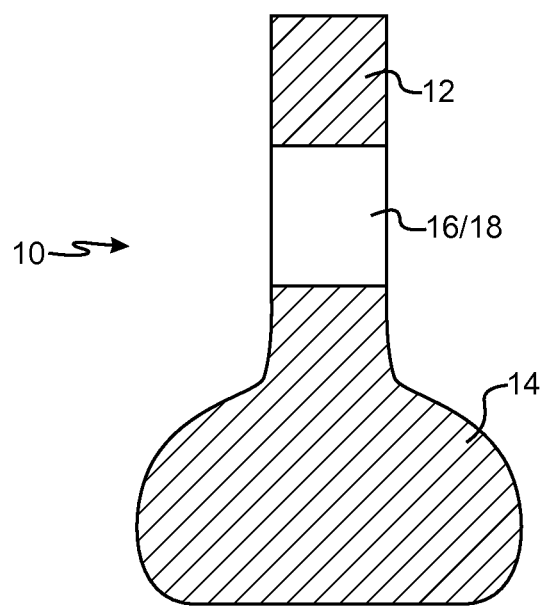

In the embodiment of hand-held atrial fibrillation detection device 10 shown in FIG. 10, device 10 comprises a housing 16 configured to sit upright on a flat surface such as a table top, and has electrodes 12 and 14 disposed at opposite ends thereof, where electrodes 12 and 14 are configured for a patient to hold in his or her hands. Light pipe 18 is again formed from a semi-transparent or transparent polymer, and permits light emitted by red and green LEDs located within housing 16 and/or light pipe 18 to be transmitted therethrough for viewing by a patient or physician.

Figure 11:
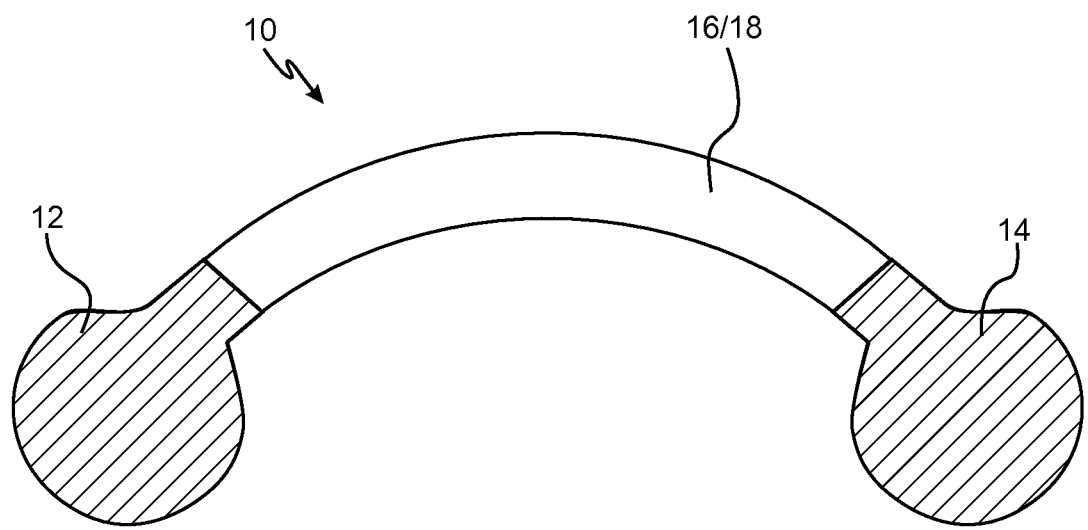

In the embodiment of hand-held atrial fibrillation detection device 10 shown in FIG. 11, device 10 comprises an elongate curved and cylindrically-shaped housing 16 having bulbous electrodes 12 and 14 disposed at opposite ends thereof, where electrodes 12 and 14 are configured for a patient to hold in his or her hands. Light pipe 18 is formed from a semi-transparent or transparent polymer, and permits light emitted by red and green LEDs located within housing 16 and/or light pipe 18 to be transmitted therethrough for viewing by a patient or physician.

Figure 12:
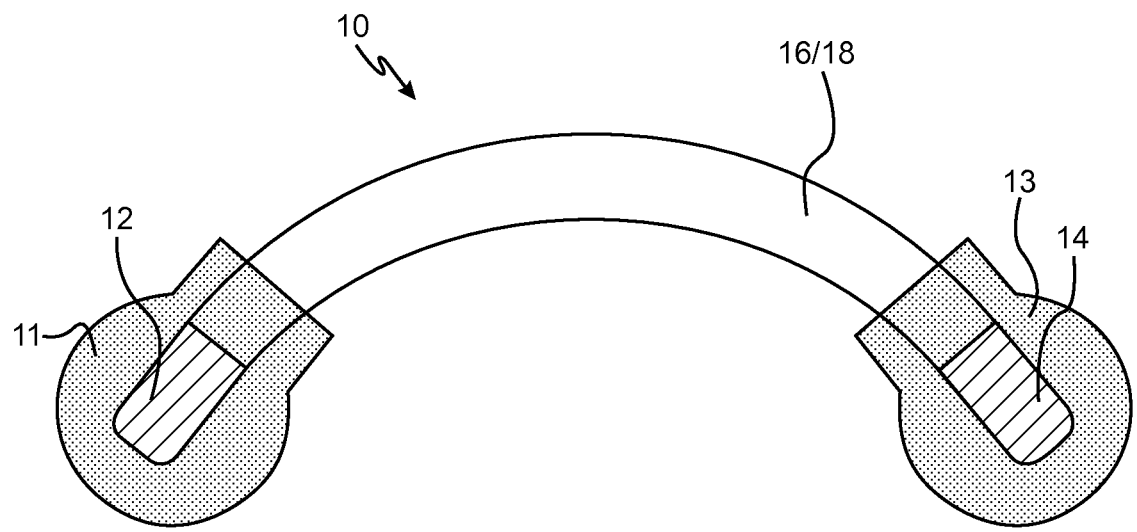

In the embodiment of hand-held atrial fibrillation detection device 10 shown in FIG. 12, device 10 comprises an elongate curved and cylindrically-shaped housing 16 having electrodes 12 and 14 disposed at opposite ends thereof, and where electrodes 12 and 14 are covered by bulbous-shaped electrically conductive electrode cover 11 and electrically conductive electrode cover 13. Covers 11 and 13 are formed of a compressible and electrically conductive material that conforms to the shape of the patient's hands during use.

Figure 13:
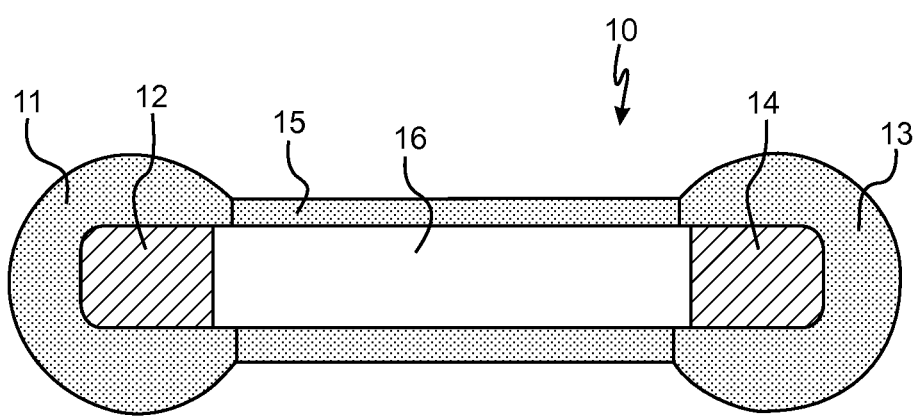

In the embodiment of hand-held atrial fibrillation detection device 10 shown in FIG. 13, device 10 comprises elongate and cylindrically-shaped housing 16 having electrodes 12 and 14 disposed at opposite ends thereof, and where electrodes 12 and 14 are covered by bulbous-shaped electrically conductive electrode cover 11 and electrically conductive electrode cover 13. Covers 11 and 13 are formed of a compressible and electrically conductive material that conforms to the shape of the patient's hands during use, and covers 11 and 13 are separated by electrically insulative cover 15, which may have ports or openings disposed therethrough that permit the passage of light emitted by LEDs or visual indicators 20 therethrough. Note that according to one embodiment the electronics associated with device 10 may be located within a protective pouch disposed within housing 16. To avoid unnecessary detail, note further that not all electrical and mechanical connections and features corresponding to device 10 are shown in the Figures.

Figure 14:
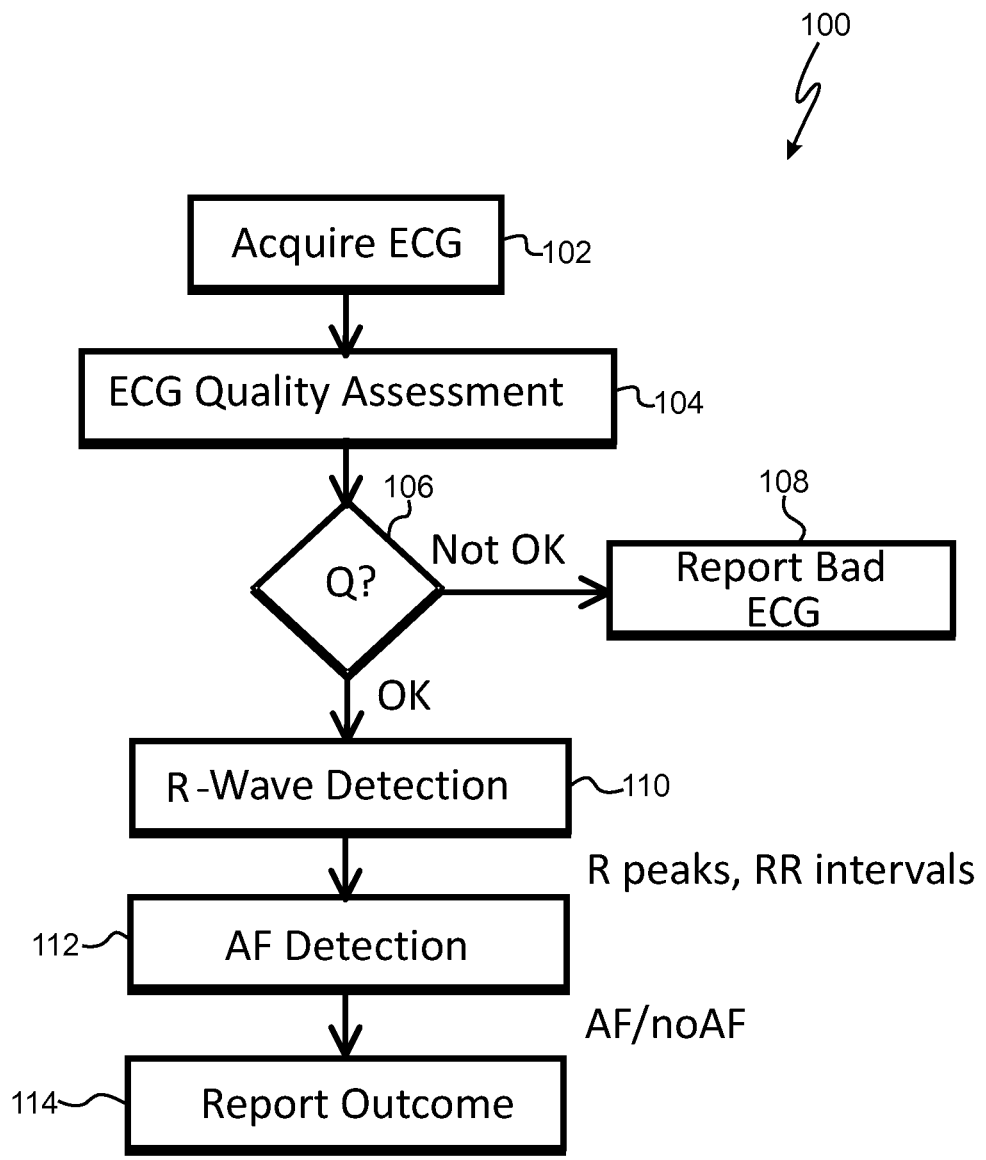
FIG. 14 shows one embodiment of a high-level method for detecting atrial fibrillation in a patient using an atrial fibrillation detection device.

Referring now to FIG. 14, there is shown one embodiment of high-level method 100 for detecting atrial fibrillation in a patient using device 10. At step 102, the patient's ECG is acquired. At step 104, the quality of the acquired ECG is assessed by device 10. At step 106, it is determined whether the ECG is of suitably high quality, or not (step 108). If the ECG is of sufficiently high quality, it is passed on to step 110, where R-waves associated with the ECG are detected. At step 112, and on the basis of the R-waves that have been detected by device 10, atrial fibrillation in the ECGs is detected (or not). The outcome of the atrial fibrillation analysis of the R-waves is reported at step 114.

Figure 15:
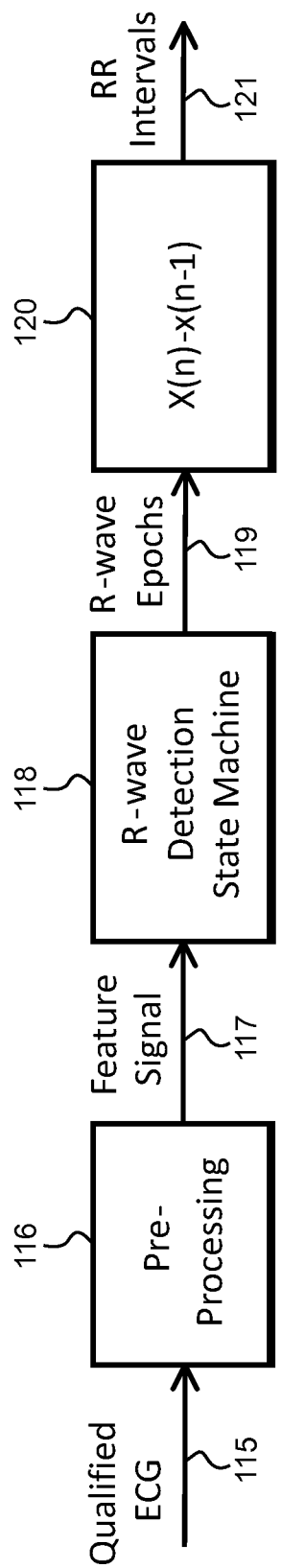
FIG. 15 shows details according to one embodiment of determining R-R intervals.
Figure 16:
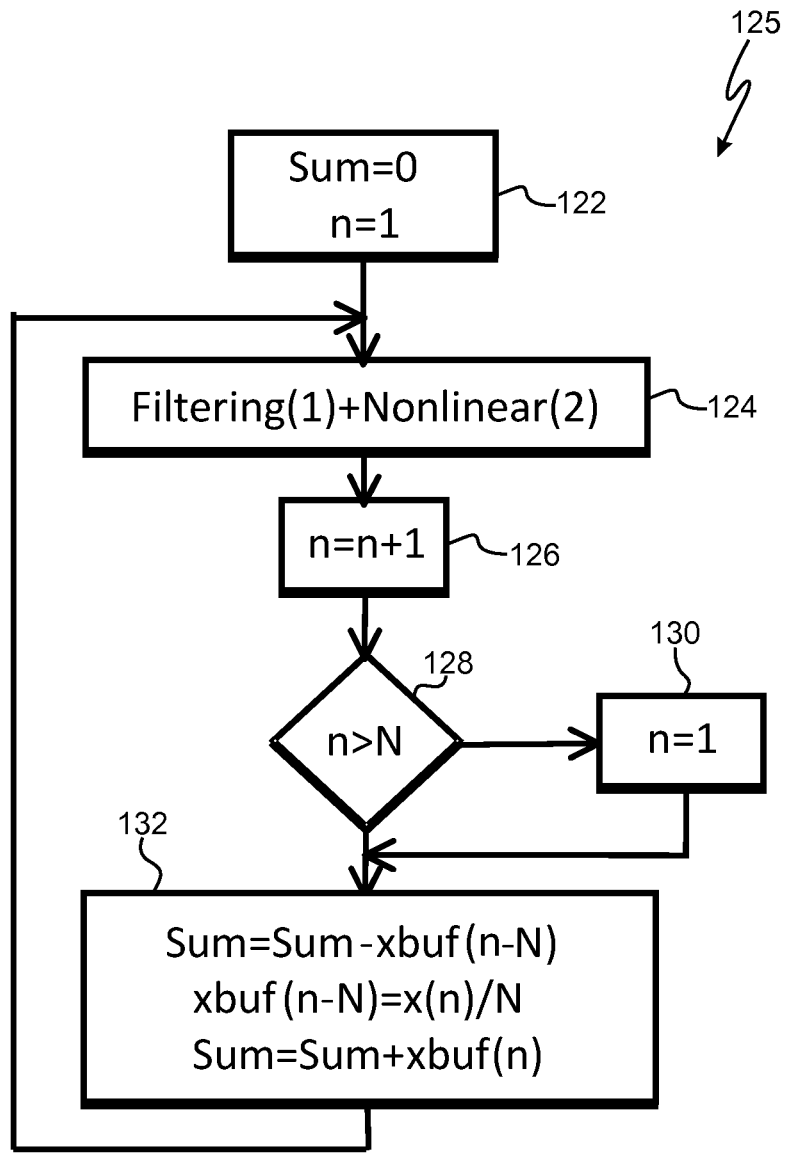
FIG. 16 show portions of methods for detecting R-waves.

FIG. 15 shows a portion of method 100 of FIG. 14, and is directed in particular to step 110 thereof (R-wave Detection). At step 116, an ECG that has passed through step 106 of FIG. 14 as an "OK" ECG (or suitably high quality ECG) is passed on to step 116 of FIG. 15 for ECG pre-processing. According to one embodiment, pre-processing of a qualified ECG is carried out to generate a "feature signal", and comprises band-pass filtering and differentiation of the ECG, followed by carrying out a non-linear expansion operation, and then a moving average operation before the pre-processed ECG is passed on to an R-wave detection state machine at step 118. According to one embodiment, pre-processing at step 116 begins with a band-pass filtering and differentiating operation defined by the equation:

$$y(n) = \frac{\sum_{k=0}^{K} b_k x(n-k) - \sum_{m=0}^{M} a_m y(n-m)}{a_0}$$

where a=[6, −9, 4] and b=[−1, −2, 1, 4, 1, −2, −1]. According to one embodiment, and by way of non-limiting illustrative example only, the band-pass filtering and differentiating operation is followed by a non-linear expansion operation defined by the equation:

Next, a recursive moving average filter is applied to the processed ECG data, as shown in method 125 of FIG. 16. The recursive moving average filter operation of FIG. 16 generates feature signal (117). Next, the pre-processed ECG data (feature signal 117 of FIG. 15) are forwarded to the R-wave detection state machine at 118, where R-wave epochs (119) are generated for use in the calculation of R-R intervals (121 of FIG. 15).

According to one embodiment, during R-wave detection and classification (see peak detection state machine 118 of FIG. 15), R-waves are sorted according to four different states: (1) R-wave detection blanking period timed out; (2) R-wave detection threshold exceeded; (3) R-wave peak fraction not met; and (4) Blanked for R-wave detection. The parameters utilized for each of these R-wave categories for states (1) through (4), respectively, are: (a) K1: Fraction of the peak amplitude that the feature signal must go below to confirm R-wave detection (b) K2: Fraction of the peak amplitude used to calculate a new detection threshold value; (c) THT-MIN: Minimum detection threshold (mV), and (d) TBLANKING: Blanking period (msec). State 1 of the R-wave detector state machine is initially entered each time after the R-wave detection blanking timer times out following previous R-wave detection. In this state, the R-wave detector is waiting for the feature signal (117) to exceed the current threshold. If this occurs, the state machine moves to state 2 (threshold exceeded). In this state, the maximum amplitude (i.e. the peak amplitude) of the feature signal is determined until the feature signal goes below a fraction K1 of the peak amplitude of the feature signal. At that moment in time, the threshold is adapted to another fraction K2 times (*) the determined or found peak amplitude and the state machine moves to state 3, confirming R-wave detection. After R-wave detection (state 3), the R-wave detection state machine moves directly to state 4 (Blanked for R-wave detection) and a counter is started that counts from a predefined value (TBLANKING) down to zero. When zero is reached, the state machine moves from state 4 back to state 1, thereby restarting the detection cycle.

Figure 17:
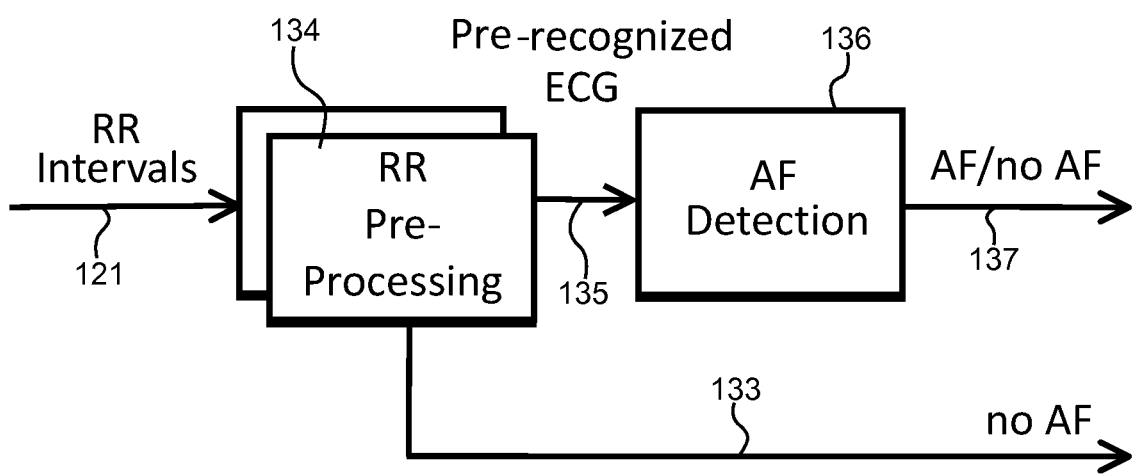
FIG. 17 shows one embodiment of R-R interval preprocessing in combination with an AF detection block/circuitry.

Referring now to FIG. 17 and FIG. 18(*b*), a short R-R interval in FIG. 18(*a*) has been removed according to the equation RR<MINRR, where the R-R intervals of FIG. 18(*b*) conform to a rule where new R-R intervals (i.e., FIG. 18(*b*)) are the sum of a short interval preceding or following another "normal" R-R interval. Removing R-R intervals that are too short reduces the effects of noise on acquired ECGs. In such a manner, the selected R-R intervals remain closest to detected mean intervals. Similarly, R-R intervals that are too long are also removed (i.e. where RR>MAXRR).

Figure 19:
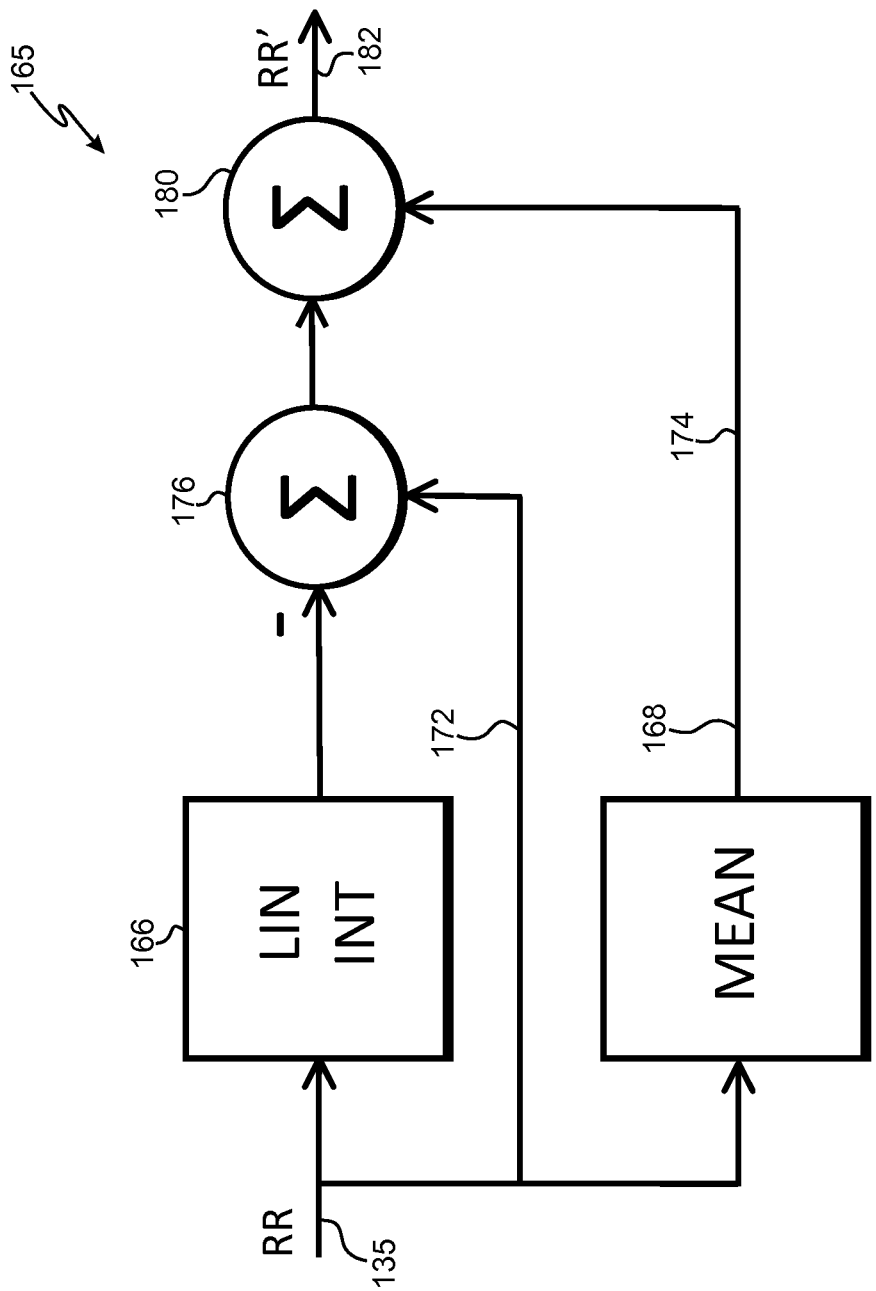
FIG. 19 illustrates one embodiment of a block diagram or circuitry employed to remove R-R interval trends from R-R intervals.

R-R intervals are further pre-processed (see 134 in FIG. 17) by removing upward or downward trends in R-R intervals (see FIG. 19) from such data by subtracting linearly interpolated R-R interval data at 166 from R-R interval data at step 180. After correction for mean R-R interval 174, trend-shifted R-R interval data are output at 182.

Figure 20:
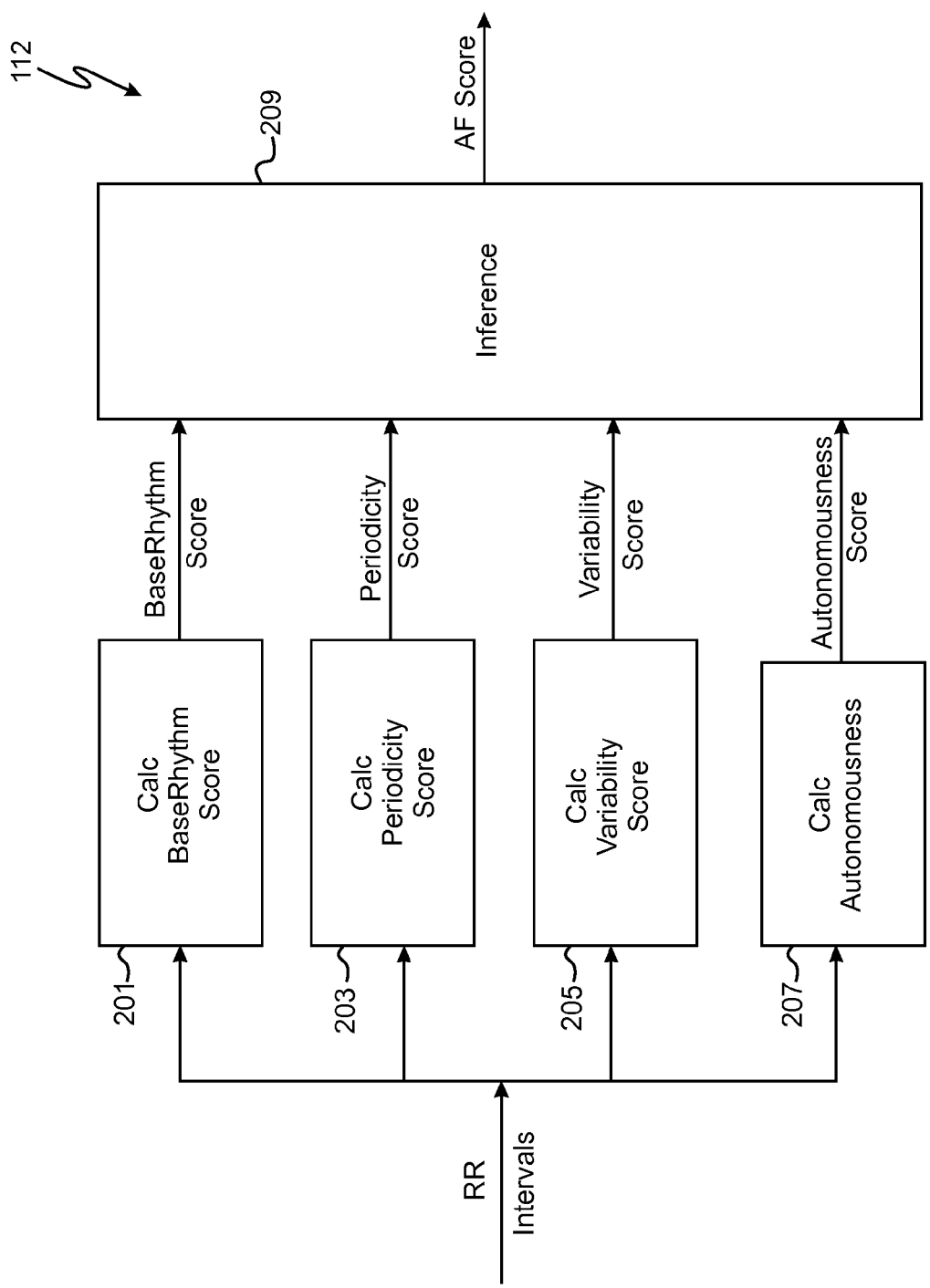
FIG. 20 shows further details according to one embodiment of determining an AF score on the basis of R-R intervals.

FIG. 20 shows further details according to one embodiment of step or circuitry 112 in FIG. 14, where an AF score is developed based on R-R intervals input thereto from step/circuitry 110. R-R intervals are analyzed in blocks 201 (Calculate Base Rhythm Score), 203 (Calculate Periodicity Score), 205 (Calculate Variability Score) and 207 (Calculate Autonomousness). Scores for each of steps/circuitry 201, 203, 205 and 207 are then forwarded to step/circuitry 209, where an overall inference or AF score is calculated. The AF score indicates whether or not a patient whose ECGs have been acquired and analyzed by device 10 has atrial fibrillation (AF). More about FIG. 20 is said below.

Figure 21:
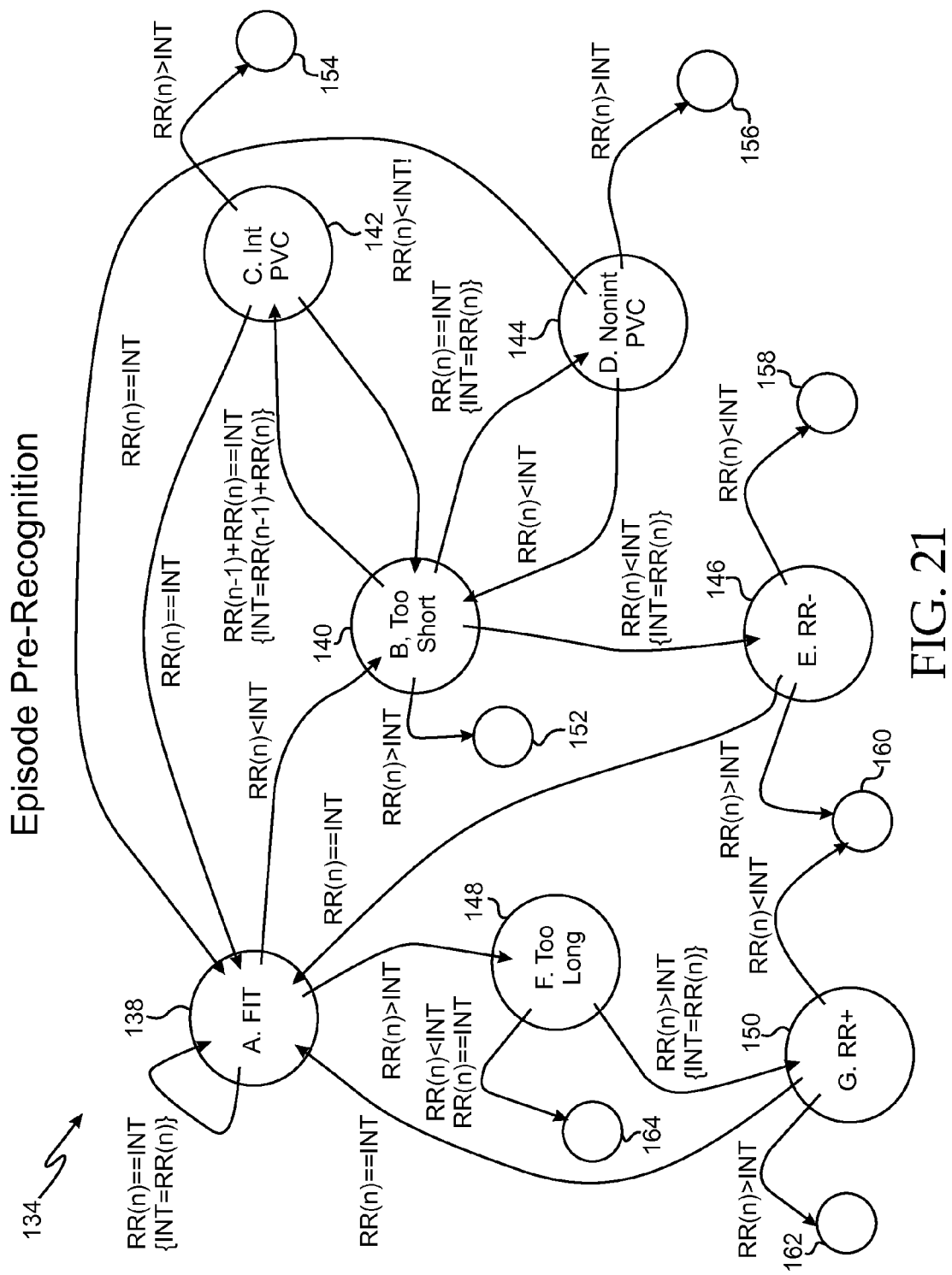
FIG. 21 illustrates one embodiment of a an episode base rhythm recognition state machine.

Referring now to FIG. 21, there is shown one embodiment illustrating calculation of the base rhythm score by state machine 134. In FIG. 21, the illustrated state diagram implements a base rhythm recognition algorithm configured to detect non-AF episodes. Normal rhythms, interrupted by one or more episodes such as interpolated or non-interpolated premature ventricular contractions (i.e., intPVC or nonintPVC) are characterized by rate increases (RR⁻) and rate decreases (RR⁺) that are recognized by moving from state to state. The state-machine shown in FIG. 21 remains in the same state in between beats. State-transitions may be made at each R-wave detection time interval R(n), taking the last R-R interval RR(n)=R(n)−R(n−1) into account to determine at each state (states A through G) what the next state will be. At all times, a test interval (INT) is defined, starting with the first interval that can be updated during state transitions (including moving from state A and back to state A). During stable rhythms, the base rhythm recognition state machine 134 remains in state A, symbolized by the arrow labeled RR(n)== INT, starting and ending at state A. If the interval RR(n) 'equals' the test interval, the state machine remains in state A. In this context, 'equal' (or ==) means that a relative or absolute deviation (K % or M msec) is allowed in an interval RR(n) but is nevertheless still considered as being "equal."

Figure 22:
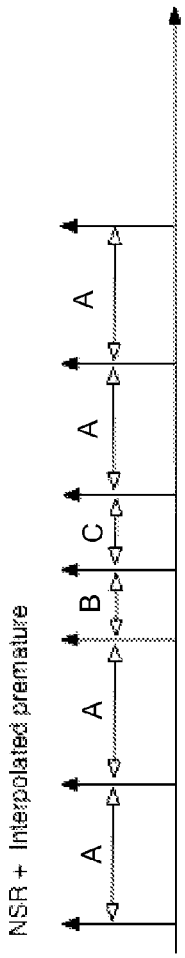
Figure 23:
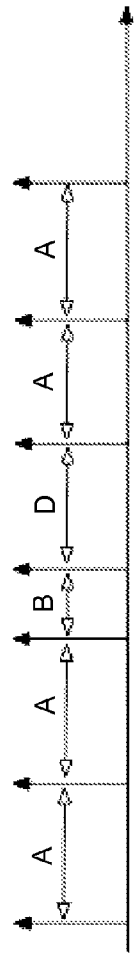
Figure 24:
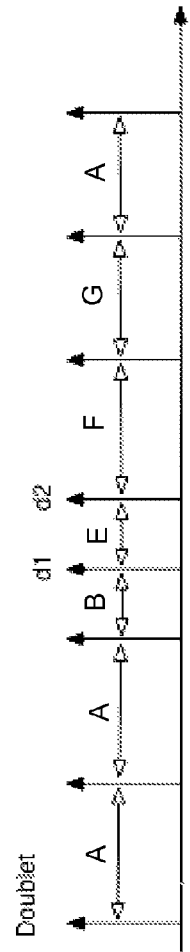
Figure 25:
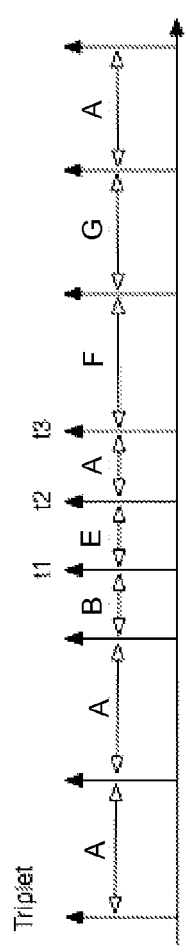
Figure 26:
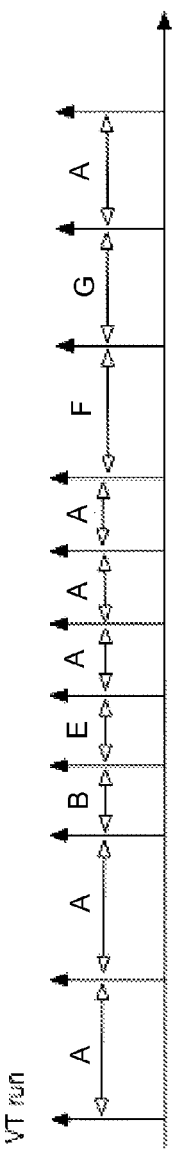

If a short interval is encountered where the condition RR(n) <INT is true, state machine 134 moves from state A (138) to state B (140) (see FIG. 22). From state B or 140, the next interval is processed. If the sum of interval RR(n) and previous interval RR(n−1) equals INT, state machine 134 moves to state C (or 142), which is indicative of an interpolated PVC (see FIG. 22). The test interval INT is then updated {INT=RR (n−1)+RR(n)}. If however, while in state B the next interval 'equals' INT, the state machine moves to state D (non-interpolated PVC). The test interval INT is then updated {INT=RR(n)}, (see FIG. 23). If while in state C or state D the new interval RR(n) is again too short, the state machine moves back to state B. Doublet ECG signals, triplet ECG signals and (short) VT ECG signals then become state sequences as shown in FIGS. 24, 25 and 26. A normal sinus rhythm followed by a lower rate ECG signal initiates an A-state sequence followed by states F, G (see FIG. 27). Various combinations of normal sinus rhythms, PVCs, rate increases and decreases can be coded by chains of state transitions (see FIGS. 28, 29 and 30). Non-facilitated or unrecognized R-R sequences lead to breaking such chains at 152, 154, 156, 158, 160 or 162) and a restart of the state machine at state A. In such a manner, evaluation of a sequence of R-R intervals corresponding to the patient's acquired ECG signals creates one or more chains of state machine data of variable length.

Stable cardiac rhythms interrupted by expected patterns such as PVCs, rate increases and rate decreases create a long single chain of state machine data. In contrast, variable cardiac rhythms create more and shorter chains of state machine data. A low number of long chains are indicative of the presence of a base rhythm. On the other hand, a high number of short chains indicate the presence of a base rhythm representative of AF (or an AF condition for the patient). During AF, short multiple chains (e.g., 15-30 chains) consisting of 5-10 beats are typically found.

Still referring to FIG. 17, R-R intervals provided by x(n)−x(n−1) state machine 120 in FIG. 15 are provided as inputs to the base rhythm state machine 134. As shown in FIG. 21, R-R intervals are first input to step A (Fit) to determine whether a new R-R interval (RR(n)==INT) is 'equal' to a previously analyzed R-R interval or not. In this context, 'equal' means equal within a range of acceptance, i.e., equal to K % of normal relative or M msec absolute variation due to autonomic regulation. Typically, K is 10%, but this figure may be adapted to optimize the allowed RR variation per patient during episodes of normal sinus rhythm. If the new R-R interval is greater than the test interval (INT), the state machine goes from state A to state B or 140 ("Too Short"). If the new R-R interval is less than the test interval (INT), the new R-R interval is sent to state F or 148 ("Too Long"). At steps 140 and 148, the newly presented R-R interval is analyzed once again to determine whether it is greater than or less than the test interval (INT). If the new R-R interval at step 148 is equal to the test interval (INT), the analysis is terminated at step 168. If the new R-R interval at step 148 is greater than the test interval (INT), the analysis continues at step 150 (G or "RR⁺"), where a determination is made as to whether (R-R(n)) is greater than (INT) (at which point further analysis is terminated) or less than INT (at which point further analysis is also terminated). If the new R-R interval (RR(n)) at step 140 is greater than the test interval (INT), the analysis is terminated at step 152. If the new R-R interval (RR(n)) at step 140 is less than the test interval (INT), the analysis continues at step 146 (E or RR), where a determination is made as to whether RR(n) is greater than (INT) (at which point further analysis is terminated at step 160) or less than INT (at which point further analysis is also terminated at step 158). If the new R-R interval RR(n) at step 140 is exactly equal to the previously analyzed RR interval INT, the analysis continues at step 144 (D or Nonint PVC), where a determination is made as to whether RR(n) is greater than (INT) (at which point further analysis is terminated at step 156) or less than INT (at which point analysis is continued at step 138 (A or Fit). Moreover, if at step 140 the sum of the new R-R interval (RR(n)) and the previously analyzed interval (RR(n−1)) is exactly equal to INT, the analysis continues at step 142 (C or Int PVC), where a determination is made as to whether such sum is greater than (INT) (at which point further analysis is terminated at step 154) or less than INT (at which point analysis is continued at step 138 (A or Fit). Base rhythm state machine 134 thus arrives at determinations of which R-R intervals indicate the lack of presence of a base rhythm characteristic of atrial fibrillation.

According to one embodiment of methods and devices corresponding to the Base Rhythm State Machine of FIG. 21, provided below is computer pseudo-code corresponding thereto.

TABLE 1

Computer Pseudo-Code Corresponding to the Operation of a One Embodiment of a Base Rhythm State Machine

```
% CALL
% [chain,type]=findbaseRhythm_sm(RR,M)
%
% DESCRIPTION
% RR    RR interval vector (ms)
% M     Range of allowance of beat to beat variation (fraction)
% PLOT  Plot on/off
%
% chain  Array of cells of indices chained intervals
% type   Array of cells of types of chained intervals
%
% IDENTIFICATION
% Richard Houben, Applied Biomedical Systems BV
%
function [chain,type]=findbaseRhythm_state(RR,M,PLOT)
% 1. Initialize
```

TABLE 1-continued

Computer Pseudo-Code Corresponding to the Operation
of a One Embodiment of a Base Rhythm State Machine

```
chainNum=1;                          % Chain number
chainIdx=1;                          % Chain index
chain{chainNum,chainIdx}=1;type{chainNum,chainIdx}=1;
chainIdx=chainIdx+1;
n=2;                                 % RR interval index
INT=RR(1);                           % Test interval
aINT(1)=INT;
state=1;
while 1
    % Termination condition
    if PLOT; aINT(n)=INT; end
    if n>length(RR); break ; end
    switch state
        case 1 % Fit
            if EQ(RR(n),INT,M)
                state=1;             INT=RR(n);
            elseif LT(RR(n),INT,M)
                state=2;
            elseif GT(RR(n),INT,M)
                state=6;
            end
        case 2 % Too Short
            if EQ(RR(n-1)+RR(n),INT,M)
                state=3;             INT=RR(n-1)+RR(n);
            elseif EQ(RR(n),INT,M+0.1)
                state=4;             INT=RR(n);
            elseif LT(RR(n),INT,M)
                state=5;             INT=RR(n);
            elseif GT(RR(n),INT,M)
                state=-2;
            end
        case 3 % PVCi
            if LT(RR(n),INT,M)
                state=2;
            elseif EQ(RR(n),INT,M)
                state=1;
            elseif GT(RR(n),INT,M)
                state=-3;
            end
        case 4 % PVCni
            if LT(RR(n),INT,M)
                state=2;
            elseif EQ(RR(n),INT,M)
                state=1;
            elseif GT(RR(n),INT,M)
                state=-4;
            end
        case 5 % RR-
            if EQ(RR(n),INT,M)
                state=1;
            elseif GT(RR(n),INT,M)
                state=-5;
            elseif LT(RR(n),INT,M)
                state=-5;
            end
        case 6 % Too long
            if EQ(RR(n),INT,M)
                state=-6;
            elseif GT(RR(n),INT,M)
                state=7;             INT=RR(n);
            elseif LT(RR(n),INT,M)
                state=-6;
            end
        case 7 % RR+
            if EQ(RR(n),INT,M)
                state=1;
            elseif LT(RR(n),INT,M)
                state=-7;
            elseif GT(RR(n),INT,M)
                state=-7;
            end
    end
    % Update chain
    if state>0
        % Add to chain
        chain{chainNum,chainIdx}=n;
        type{chainNum,chainIdx}=state;
        chainIdx=chainIdx+1;
        n=n+1;
    else
        % Terminate chain
        chain{chainNum,chainIdx}=n;
        type{chainNum,chainIdx}=state;
        % Initiate new chain
        state=1;
        chainNum=chainNum+1;
        chainIdx=1;
        chain{chainNum,chainIdx}=n;
        type{chainNum,chainIdx}=state;
        chainIdx=chainIdx+1;
        n=n+1;if n>length(RR); break ; end
        INT=RR(n);
    end
end
function k=EQ(RR,INT,M); k=(RR>=INT*(1-M) & RR<=INT*(1+M));
function k=GT(RR,INT,M); k= RR>(INT*(1+M*2));
function k=LT(RR,INT,M); k= RR<(INT*(1-M));
```

Figure 31:
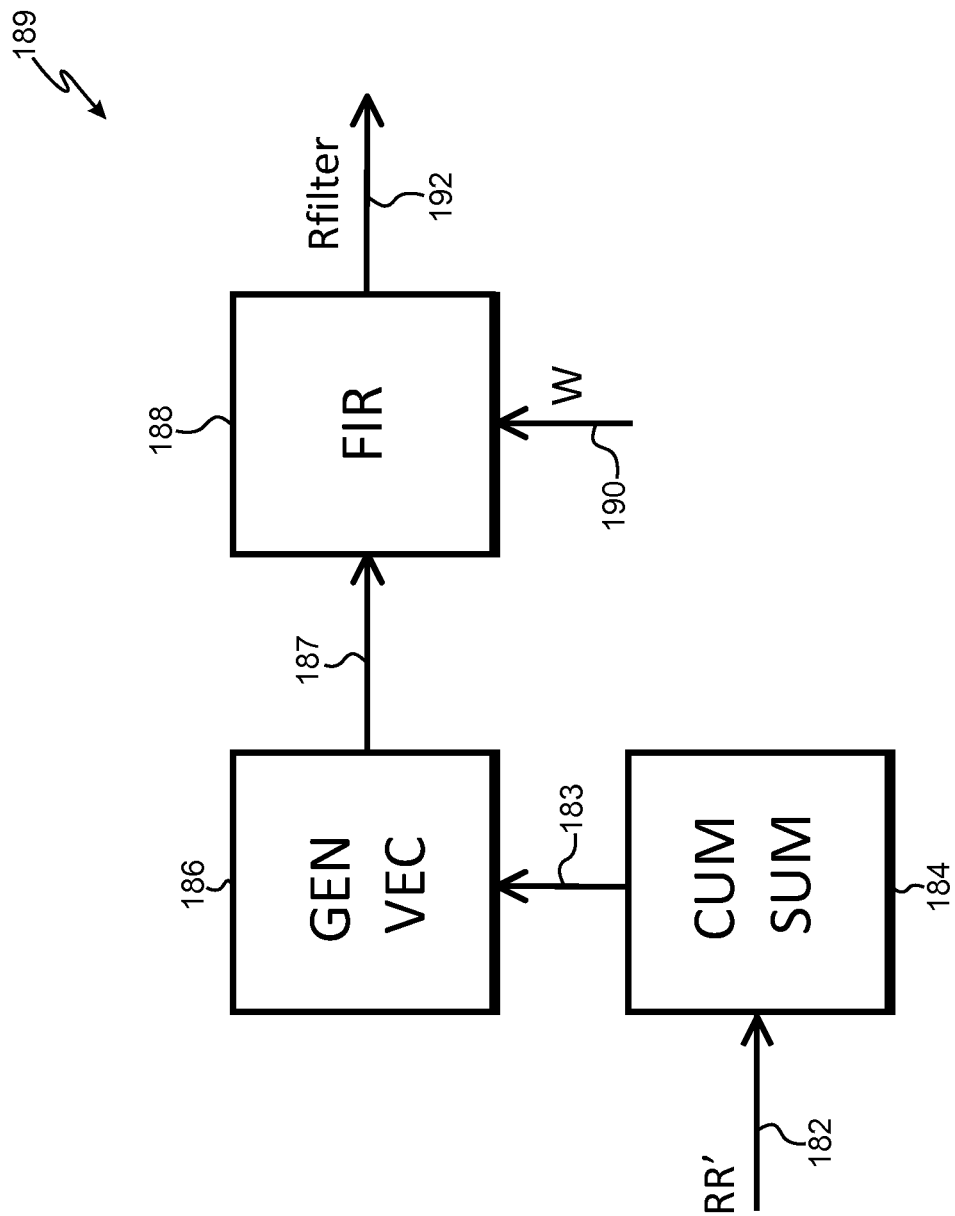
FIG. 31 shows further steps according to one embodiment for calculating periodicity and/or variability scores.
Figure 32:
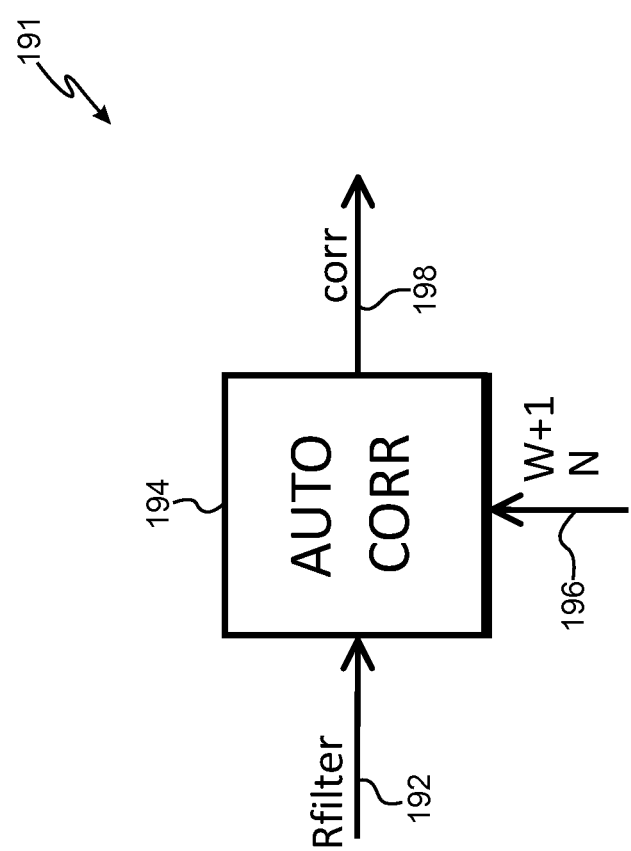
FIG. 32 shows one embodiment of autocorrelation block diagram or circuitry.
Figure 33:
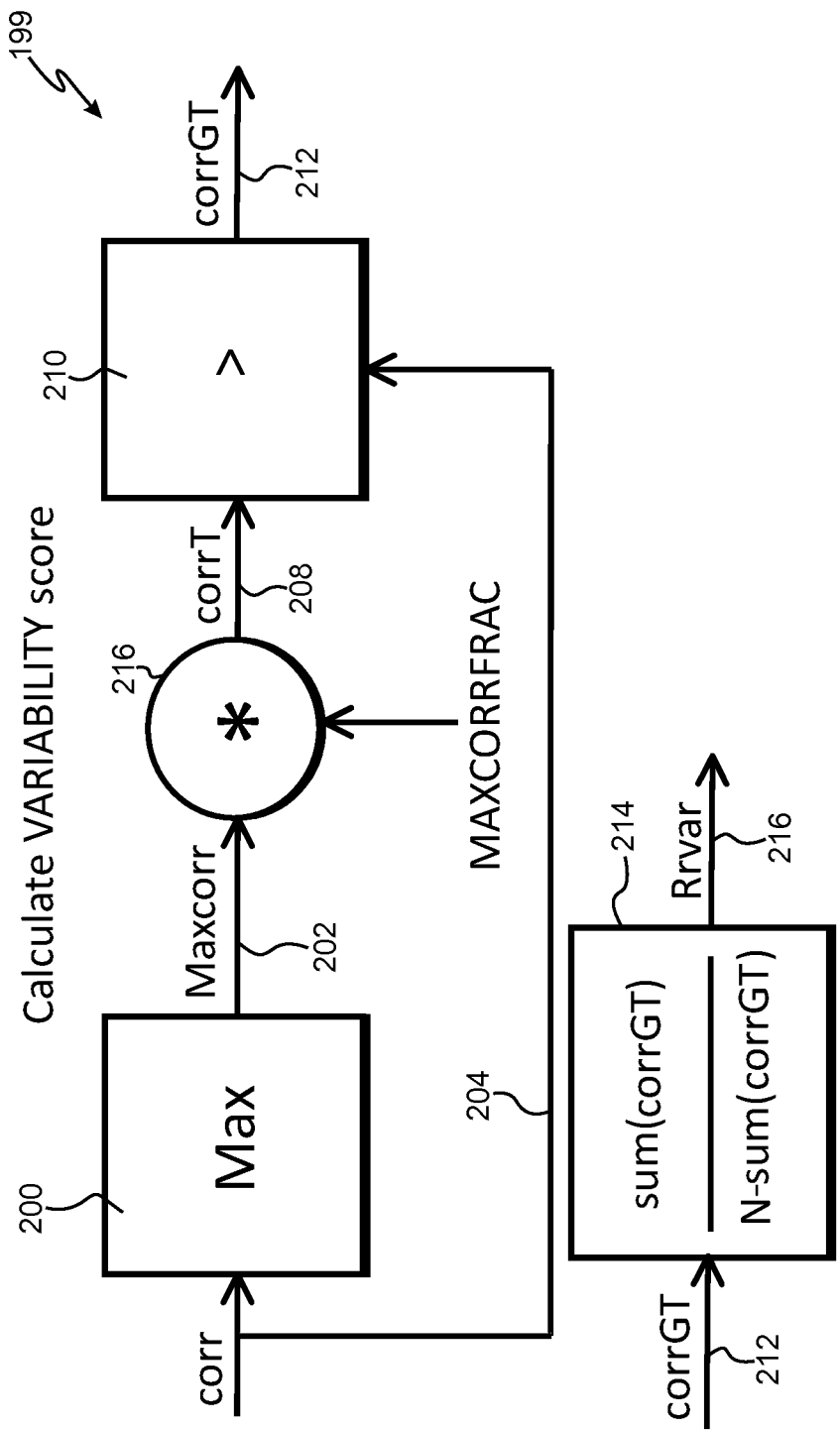
FIG. 33 shows one embodiment of a block diagram or circuitry for processing autocorrelation data.
Figure 34:
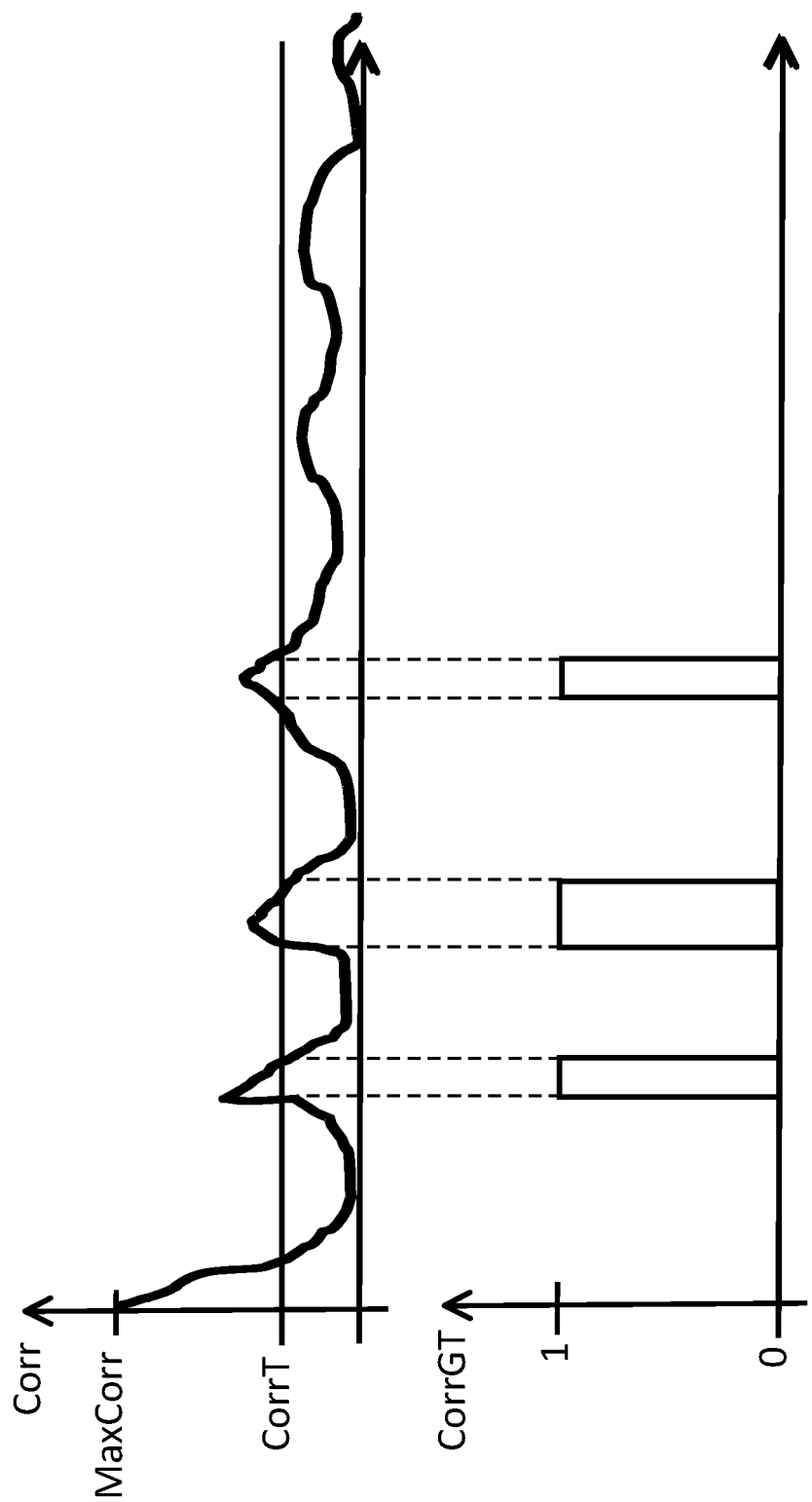
FIG. 34 shows an illustrative example of calculating a periodicity or variability score.

FIG. 31 shows further steps according to one embodiment for calculating variability and/or periodicity scores, where linearized, corrected or trend-shifted R-R interval data are input to step 184 and a vector of ones and zeros is generated with W ones following each detected R-wave epoch using a W-tap finite impulse response filter (FIR, 188) to generate an output Rfilter. FIG. 32 shows an autocorrelation step/circuitry 194, which auto-correlates the Rfilter data to provide correlated output data 198, which are calculated in steps of W+1 samples over N steps using the Rfilter data as inputs. Next, and as shown in FIG. 33, in one embodiment correlated output data 198 are input to method/circuitry 199 to generate a calculated R-R variability score (RRvar) as a fraction of time the correlation function exceeds a MAXCORRFRAC of the maximum correlation value that is determined. An illustrative example of calculating a periodicity or variability score is shown in FIG. 34, where output CorrGT (the output provided by method/circuitry 199 of FIG. 33) corresponds to those portions of Corr exceeding CorrT. Stable cardiac rhythms create a peak R-R autocorrelation function (Corr) occasionally exceeding CorrT, whereas variable cardiac rhythms such as AF create a more continuous decaying R-R autocorrelation function with more and longer portions exceeding CorrT and therefore a higher RRvar (see 216 in FIG. 33).

Figure 35:
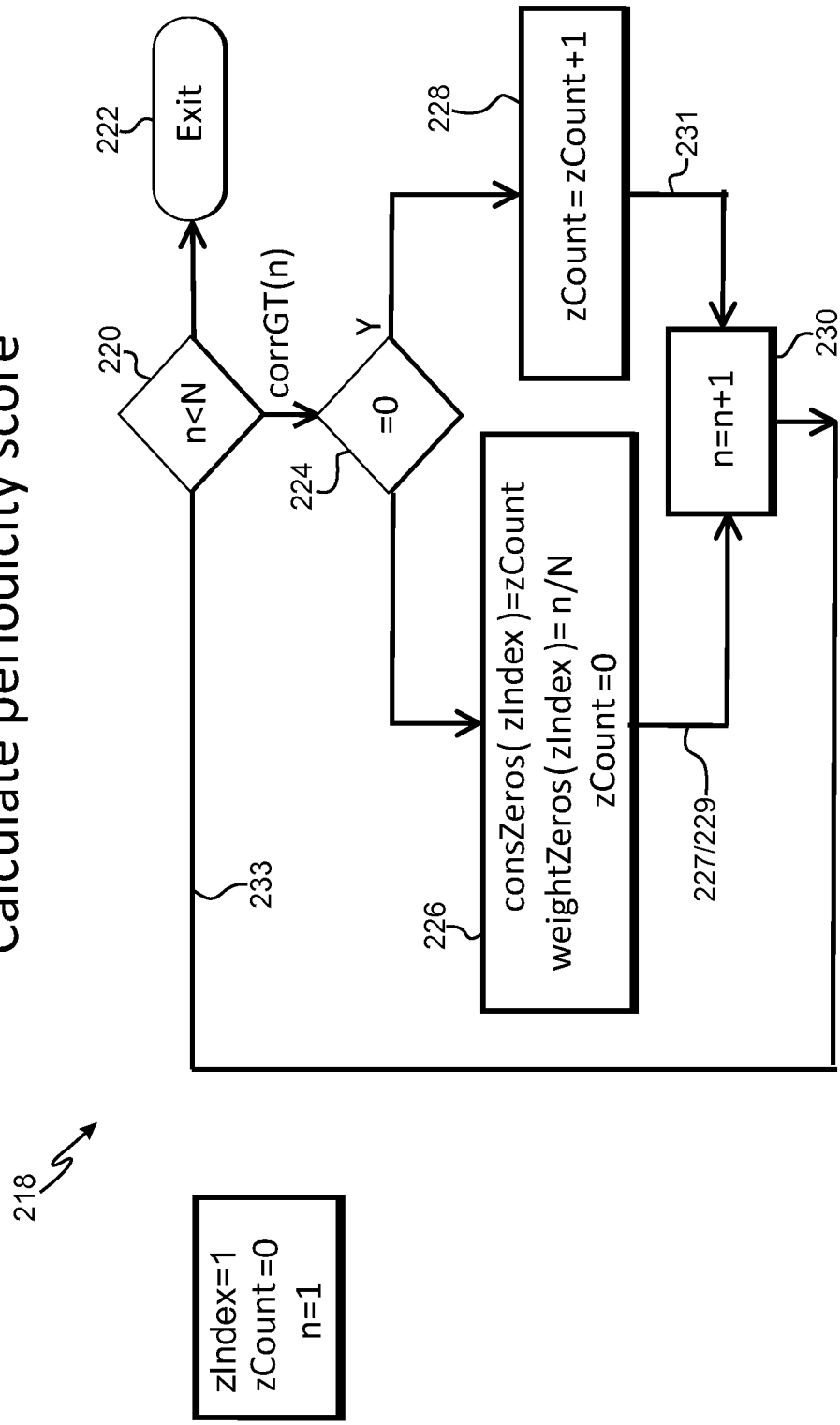
FIGS. 35 and 36 illustrate one embodiment of a further method for calculating a periodicity score.
Figure 36:
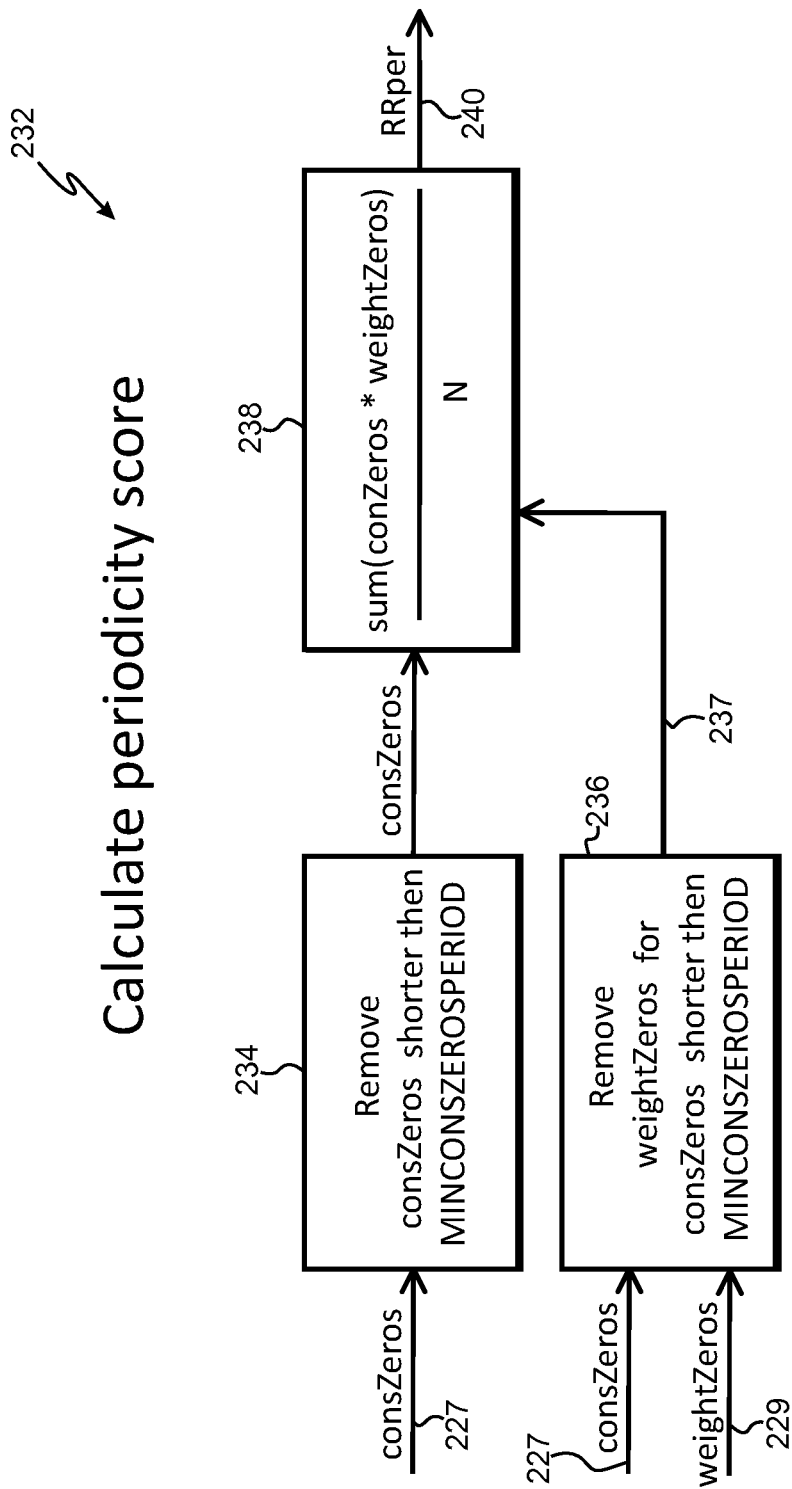

FIGS. 35 and 36 illustrate one embodiment of a further method for calculating a periodicity score. CorrGT of a periodic RR interval sequence, related to normal sinus rhythm shows short portions of Corr exceeding CorrT separated by longer non-correlating episodes, where Corr≤CorrT. In FIG. 35, the number of consecutive of zeros (Corr≤CorrT) in CorrGT (consZeros) are counted. Also, weight values (consWeight) that taper down for episodes corresponding to zeroes found at larger correlation lags are created. In FIG. 36, sequences of consecutive zeroes shorter than MINCONZEROSPERIOD are removed, before the quantity RRper is calculated as a function of the fraction of remaining consecutive zeros (consZeros) times (*) weightZeros (237) and the sequence of N samples in the sequence.

Referring to FIG. 20 (207), according to one embodiment the autonomousness score is calculated based on the R-R intervals by quantifying the amount of heart rate variability specifically induced by the respiratory system and baroreflex, which is one of the body's homeostatic mechanisms for maintaining blood pressure that can be observed during normal sinus rhythm. In one embodiment, power spectral analysis is used to calculate the presence and amount of the respiratory artifact within the frequency band from 0.2-0.4 Hz, reflecting breathing rate and the baroreflex, which typically peak between 0.05-0.15 Hz. In another embodiment, time domain heart rate variability methods and deceleration capacity are used to analyze R-R sequences quantifying the influence of the autonomic nerve system that can be observed during normal sinus rhythm but not during AF.

Next, and according to one embodiment, the AF score is generated according to the equation:

$$AFScore=(3*variabilityScore-periodicyScore-2*baseRhythmScore)/3$$

The resulting AFScore is compared against a predetermined threshold to arrive at a final determination of whether or not the patient has AF. According to one embodiment, such a predetermined threshold ranges between about −1.0 and about 1.0. Typically, and in one embodiment, an AF threshold value of 0.15 is used. A lower threshold makes detection more sensitive at the expense of specificity, and vice-versa. If the AFScore is below the predetermined threshold, then an AF episode has not been detected, and the patient is deemed not to have AF. If the AFScore is above the predetermined threshold, then an AF episode has been detected, and the patient is determined to have AF. Note that fuzzy logic, artificial neural networks (ANN), support vector machines (SVM) and other computational methods may be employed to arrive at such a final determination of AF or No AF.

Figure 37:
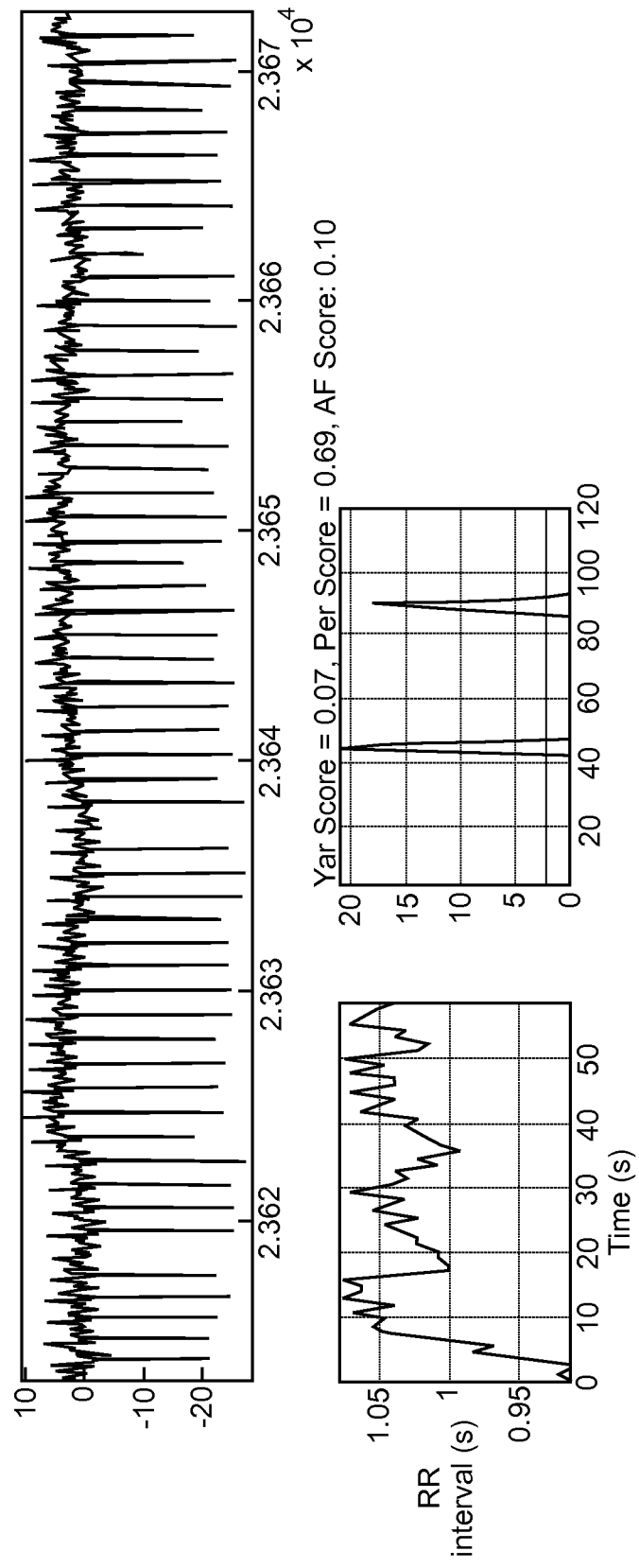
FIG. 37 shows one example of a series of R-waves detected in a patient's ECG during an episode of normal cardiac sinus rhythm (NSR), and the R-R interval sequence and autocorrelation function corresponding thereto.

Referring now to FIG. 37, there is shown in the upper panel thereof one example of a series of R-waves detected in a patient's ECG during an episode of normal cardiac sinus rhythm (NSR). In the lower left-hand panel there is shown the corresponding R-R interval sequence, while in the lower right-hand panel there is shown the corresponding autocorrelation function of the R sequence (Rfilter) that has been obtained after the R-R sequence has been regularized or linearized, and upward or downward R-R trends have been removed from the R-R intervals. As shown in FIG. 37, the variability score is 0.07 and the periodicity score is 0.69. The resulting AF score is 0.10, which is below an AF threshold of 0.15).

Figure 38:
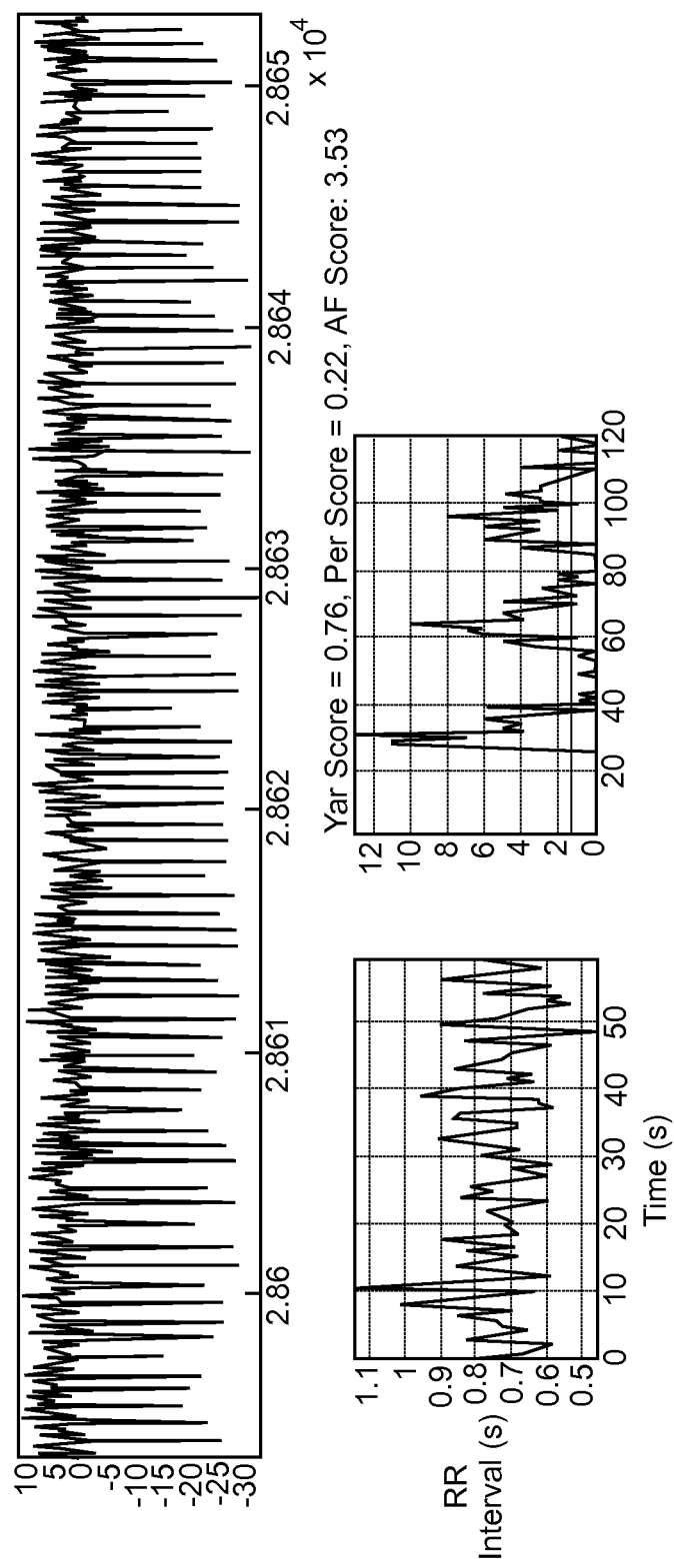
FIG. 38 shows one example of a series of R-waves detected in a patient's ECG during an episode of paroxysmal atrial fibrillation, and the R-R interval sequence and autocorrelation function corresponding thereto.

FIG. 38 shows a different example, where the upper panel thereof contains R-waves detected in a patient's ECG during an episode of paroxysmal atrial fibrillation. In the lower left-hand panel there is shown the corresponding R-R interval sequence, while in the lower right-hand panel there is shown the corresponding autocorrelation function of the R sequence (Rfilter) that has been obtained after the R-R sequence has been regularized or linearized, and upward or downward R-R trends have been removed from the R-R intervals. In the example of FIG. 38, the resulting variability score is 0.76 and the periodicity score is 0.22. The resulting AF score is 3.53, which is well above the AF threshold of 0.15.

Referring now to the preceding text and diagrams, it will be that there are disclosed and described various embodiments of methods and devices for detecting atrial fibrillation in an electrocardiogram (ECG) acquired from a patient, where times corresponding to R-waves in the electrocardiogram are determined, a plurality of sequentially-ordered R-R time intervals corresponding to the R-wave times are determined, an R-R test interval (INT) is selected from among the plurality of R-R time intervals, R-R time intervals are sequentially selected and compared in a base rhythm recognition state machine to determine which of the selected R-R time intervals correspond to at least one of a predetermined number of non-atrial-fibrillation states, and at least some of the non-atrial-fibrillation states require updating of INT when R-R time intervals are compared therein. Next, it is determined which of the selected R-R time intervals correspond to a potential atrial fibrillation state, and on the basis of the selected and compared R-R time intervals, a base cardiac rhythm score is generated.

The predetermined number of non-atrial-fibrillation states may include at least one of a no-change state, a premature beat state, an interpolated premature ventricular contraction state, a non-interrupted premature ventricular contraction state, a faster rate change state, a slower rate change state, and a pause state. The R-R time intervals may be compared to INT to determine which of the selected R-R time intervals corresponds to at least one of a predetermined number of non-atrial-fibrillation states using a comparison threshold ranging between about 90% of INT and about 110% of INT when comparing each R-R time interval to INT. Determining times corresponding to R-waves in the ECG may also further comprise at least one of band-pass filtering and differentiation of the ECG, non-linear expansion filtering of the ECG, moving average filtering of the ECG, and using an R-peak detection state machine. Determining the plurality of sequentially-ordered R-R time intervals corresponding to the R-wave times may further comprise subtracting a first time marker for one R-wave from a second time marker for another R-wave. Generating the base cardiac rhythm score may further comprise detecting at least one of episodes of atrial fibrillation and episodes of non-atrial fibrillation on the basis of the selected and compared R-R time intervals. The plurality of sequentially-ordered R-R time intervals may be further processed to at least one of regularize the plurality of sequentially-ordered R-R time intervals, remove upward trends in the plurality of sequentially-ordered R-R time intervals, remove downward trends in the plurality of sequentially-ordered R-R time intervals, and generate an R-sequence function based on the sequentially-ordered R-R time intervals. As described above, the sequentially-ordered R-R time intervals may be auto-correlated, a rate estimate based on the sequentially-ordered R-R time intervals may be calculated, an R-R variability score based on the sequentially-ordered R-R time intervals may be calculated, and an R-R periodicity score based on the sequentially-ordered R-R time intervals may also be calculated.

The base cardiac rhythm score may be combined with at least one of the R-R variability score, R-R periodicity score and autonomousness score to produce an atrial fibrillation evidence score. On the basis of the atrial fibrillation evidence score it may be determined whether or not the patient has atrial fibrillation. The foregoing methods may also be carried out using a hand-held device, and the hand-held device may comprise first and second electrodes configured to sense the ECGs of the patient. The device may be configured to provide an audio or visual indication that the patient has atrial fibrillation, or does not have atrial fibrillation, after the patient's ECG has been acquired and analyzed by the device.

The components, devices, systems and methods described above may be implemented in medical diagnostic and therapeutic devices other than the specific external embodiments illustrated, for example, in FIGS. 1 through 13, and may be implemented in implantable medical devices such as pacemakers, implantable cardioverters (ICDs), implantable heart monitors or diagnostic devices, implantable loop recorders, external cardiac monitors or diagnostic devices other than those described explicitly above, and other components, devices, systems and methods that will become apparent to those skilled in the art upon having read and understood the present specification and drawings.

In some such additional embodiments, functionality similar to that depicted in FIG. 3, where electrodes 12 and 14 may be employed that are substantially equivalent or similar to external electrodes or electrodes included in implantable electrical leads.

Application of the above-described components, devices, systems and methods may be especially useful when atrial cardiograms are difficult to obtain and/or when only ventricular cardiograms are available for analysis. Examples of devices that are typically not configured to obtain atrial cardiograms are implantable loop recorders (ILR), implantable ventricular and bi-ventricular pacemakers, implantable cardioverters and defibrillators, external ventricular pacemakers, external loop recorders, and external defibrillators, and that may be modified in accordance with the teachings presented herein.

Examples of devices that typically are not configured to record electrical cardiac signals, but which measure or derive cardiac activity from other physiological sources are blood-pressure measuring instruments and devices, plethysmogram-based devices, impedance measuring instruments and devices, electronic stethoscope, and ultra-sound instruments and devices, which may be implantable or configured for external use.

The components, devices, systems and methods described above permit the presence or absence of atrial fibrillation to be determined on the basis of ventricular activity, and may be implemented in any of the foregoing devices or systems. Furthermore, and in accordance with the teachings presented herein, atrial fibrillation may be detected using any suitable source of ventricular activity information such as, by way of non-limiting example only, subsequent ventricular events or datasets of ventricular intervals provided by any communication means or stored in databases, and which can be processed locally or remotely to determine the presence, absence or degree of atrial fibrillation.

The above-described embodiments should be considered as examples of the present invention, rather than as limiting the scope of the invention. In addition to the foregoing embodiments of the invention, review of the detailed description and accompanying drawings will show that there are other embodiments of the invention. Accordingly, many combinations, permutations, variations and modifications of the foregoing embodiments of the invention not set forth explicitly herein will nevertheless fall within the scope of the invention.

We claim:

1. A device configured to detect atrial fibrillation in a patient, comprising:
    first and second electrodes configured to sense electrocardiograms (ECGs) of the patient;
    amplifier circuitry configured to receive and amplify the ECGs:
    at least one processor configured to detect times corresponding to R-waves in the ECGs, determine sequentially-ordered R-R time intervals corresponding to the R-wave times, select an R-R test interval (INT) from among the plurality of R-R time intervals, sequentially select the R-R time intervals and compare the R-R intervals in an episode base rhythm state machine to determine which of the selected R-R time intervals correspond to at least one of a predetermined number of non-atrial-fibrillation states, at least some of the non-atrial-fibrillation states requiring updating of INT when R-R time intervals are compared therein, determine which of the selected R-R time intervals correspond to a potential atrial fibrillation state, and generate, on the basis of the selected and compared R-R time intervals, base cardiac rhythm score.

2. The device of claim 1, wherein the predetermined number of non-atrial-fibrillation states includes at least one of a no-change state, a premature beat state, an interpolated premature ventricular contraction state, a non-interrupted premature ventricular contraction state, a faster rate change state, a slower rate change state, and a pause state.

3. The device of claim 1, wherein the at least one processor is further configured to use a comparison threshold ranging between about 90% of INT and about 110% of INT when comparing each R-R time interval to INT to determine which of the selected R-R time intervals corresponds to at least one of a predetermined number of non-atrial-fibrillation states.

4. The device of claim 1, wherein the at least one processor is further configured to at least one of band-pass fitter and differentiate the ECG non-linear expansion filter the ECG, moving average filter the ECG, and use an R-peak detection state machine.

5. The device of claim 1, wherein the at least one processor is further configured to subtract a first time marker for one R-wave from a second time marker for another R-wave.

6. The device of claim 1, wherein the at least one processor is further configured to generate the base cardiac rhythm score by detecting at least one of episodes of atrial fibrillation and episodes of non-atrial fibrillation on the basis of the selected and compared R-R time intervals.

7. The device of claim 1, wherein the at least one processor is further configured to process the plurality of sequentially-ordered R-R time intervals to at least one of regularize the plurality of sequentially-ordered R-R time intervals, remove upward trends in the plurality of sequentially-ordered R-R time intervals, remove downward trends in the plurality of sequentially-ordered R-R time intervals, and generate an R-sequence function based on the sequentially-ordered R-R time intervals.

8. The device of claim 1, wherein the at least one processor is further configured to at least one of auto-correlate the sequentially-ordered R-R time intervals, calculate a rate estimate based on the sequentially-ordered R-R time intervals, calculate an R-R variability score based on the sequentially-ordered R-R time intervals, and calculate an R-R periodicity score based on the sequentially-ordered R-R time intervals.

9. The device of claim 1, wherein the at least one processor is further configured to combine the base cardiac rhythm score with at least one of the R-R variability score and the R-R periodicity score to produce an atrial fibrillation evidence score.

10. The device of claim 1, wherein the at least one processor is further configured to determine on the basis of the atrial fibrillation evidence score whether or not the patient has atrial fibrillation.

11. The device of claim 1, wherein the device further comprises an elongated housing having the amplifier circuitry and processor disposed therewithin.

12. The device of claim 1, wherein the device further comprises at least one of an audio device and a visual device configured to provide an indication that the patient has atrial fibrillation.

13. The device of claim 1, further comprising at least one of an audio device and a visual device configured to provide an indication that the patient does not have atrial fibrillation.

14. The device of claim 1, wherein the device is a hand-held device.

15. The device of claim 1, wherein the device is an implantable medical device.

16. The device of claim 15, wherein the implantable medical device is one of a pacemaker, an implantable cardioverter (ICD), an implantable loop recorder, and an implantable cardiac monitor.

17. The device of claim 1, wherein the first and second electrodes form a portion of at least one implantable medical electrical lead.

18. The device of claim 1, wherein the device comprises a hand-held device configured to acquire the ECG from the patient and a computer configured to process the ECG to determine whether the patient has atrial fibrillation.

19. The device of claim 18, wherein the computer is a remote computer.

* * * * *